(12) United States Patent
Hidai et al.

(10) Patent No.: US 9,371,523 B2
(45) Date of Patent: Jun. 21, 2016

(54) CELL MIGRATION REGULATOR

(75) Inventors: Chiaki Hidai, Tokyo (JP); Hisataka Kitano, Tokyo (JP); Atsushi Mamiya, Tokyo (JP)

(73) Assignee: NIHON UNIVERSITY, Tokyo (JP)

( * ) Notice: Subject to any disclaimer, the term of this patent is extended or adjusted under 35 U.S.C. 154(b) by 0 days.

(21) Appl. No.: 13/993,511

(22) PCT Filed: Dec. 12, 2011

(86) PCT No.: PCT/JP2011/079263
§ 371 (c)(1),
(2), (4) Date: Aug. 21, 2013

(87) PCT Pub. No.: WO2012/081711
PCT Pub. Date: Jun. 21, 2012

(65) Prior Publication Data
US 2013/0330319 A1    Dec. 12, 2013

(30) Foreign Application Priority Data

Dec. 13, 2010 (JP) ................................. 2010-276777

(51) Int. Cl.
*A61K 38/00* (2006.01)
*C12N 9/64* (2006.01)
*A61K 38/48* (2006.01)

(52) U.S. Cl.
CPC ............ *C12N 9/644* (2013.01); *A61K 38/4846* (2013.01); *C12Y 304/21022* (2013.01)

(58) Field of Classification Search
CPC ....... A61K 38/36; A61K 38/17; C07K 14/745
See application file for complete search history.

(56) References Cited

U.S. PATENT DOCUMENTS

2008/0102115 A1* 5/2008 Oyhenart et al. ............. 424/457

FOREIGN PATENT DOCUMENTS

| EP | 0086627 B1 * | 8/1985 |
| EP | 1 650 302 A1 | 4/2006 |
| EP | 2 085 473 A1 | 8/2009 |
| WO | WO 96/40769 A1 | 12/1996 |
| WO | WO 02/36826 A2 | 5/2002 |
| WO | WO 2007/149406 * | 12/2007 |
| WO | WO 2008/04479 A1 | 4/2008 |

OTHER PUBLICATIONS

Gerotziafas et al., "Clinical Studies with Anticoagulants to Improve Survival in Cancer Patients," Pathophysiol. Haemost. Thromb. (2007-2008), vol. 36, p. 204-211.
Han et al., "Epidermal Growth Factor Stimulates Human Trophoblast Cell Migration through Rho A and Rho C Activation," Endocrinology (Apr. 2010), vol. 151, No. 4, pp. 1732-1742.
Hidai et al., "Cloning and characterization of development endothelial locus-1: An embryonic endothelial cell protein that binds αvβ3 integrin receptor," Genes & Development (1998), vol. 12, pp. 21-33.
Ho et al., "EGF-like domains of the Muc3 intestinal membrane-bound Mucin promote cell migration and accelerate intestinal wound healing," Gastroenterology (2004), vol. 126, No. 4, Suppl. 2, pp. A65-A66.
Rezaee et al., "Del1 mediates VSMC adhesion, migration, and proliferation through interaction with integrin αvβ3," Am. J. Physiol. Heart Circ. Physiol. (2002), vol. 282, pp. H1924-H1932.
Suzuki, K., "Coagulation Factors-Mediated Cell Activation," Nisshoketsu Kaigi (2007), vol. 21, pp. 53-61, with English Translation.
Zhong et al., "The N-terminal Epidermal Growth Factor-like Domain in Factor IX and Factor X Represents an Important Recognition Motif for Binding to Tissue Factor," The Journal of Biological Chemistry (2002), vol. 277, No. 5, pp. 3622-3631.
European Search Report issued Dec. 4, 2014 for European Application No. 11848771.9.

* cited by examiner

*Primary Examiner* — Marcela M Cordero Garcia
*Assistant Examiner* — Sergio Coffa
(74) *Attorney, Agent, or Firm* — Birch, Stewart, Kolasch & Birch, LLP

(57) ABSTRACT

The present invention provides a cell migration regulator capable of promoting or inhibiting cell migration, a method for regulating cell migration, and a pharmaceutical composition comprising such a regulator, etc. The cell migration regulator of the present invention comprises a peptide, a derivative thereof, or a salt of the peptide or the derivative, wherein the peptide comprises the full-length blood coagulation factor IX, a segment derived from the full-length blood coagulation factor IX by removal of the trypsin domain, the light chain of blood coagulation factor IX, or the EGF1 domain of blood coagulation factor IX, or the EGF3 domain of the endothelial cell locus-1 protein.

6 Claims, 5 Drawing Sheets
(3 of 5 Drawing Sheet(s) Filed in Color)

A

B

C

CELL MIGRATION REGULATOR

TECHNICAL FIELD

The present invention relates to a cell migration regulator, etc. More specifically, the present invention relates to a cell migration regulator comprising a peptide capable of promoting or inhibiting cell migration ability, etc.

BACKGROUND ART

Blood coagulation factor IX (F9) involved in hemostatic coagulation is an essential blood coagulation factor which has been known since a long time ago, and is well known as a causative protein for hemophilia. During the process of coagulation reaction, F9 is activated by being cleaved with blood coagulation factor XI (F11) into two fragments (heavy and light chains) and so on, and thereby promotes the coagulation reaction. In F9, its important segment functioning as a blood coagulation factor is the C-terminal (heavy chain) trypsin domain, whereas the functions of its N-terminal (light chain) segment have not been well known.

Clots formed by blood coagulation are composed of various proteins including blood coagulation factors. Previous studies have confirmed that neovascularization is more likely to occur within clots and that cancer patients with thrombosis have high risk of cancer metastasis (see, e.g., Non-patent Document 1; Gerotziafas G T et al., Clinical studies with anticoagulants to improve survival in cancer patients. Pathophysiol Haemost Thromb., 2008, vol. 36(3-4), p. 204-11). However, no certain conclusion has been reached as to the mechanisms or key molecules responsible for these events. Based on the statistically demonstrated relationship between clots and cancer metastasis, some attempts have been made to suppress cancer metastasis by administration of anticoagulants, and significant suppression of cancer metastasis has been confirmed. However, the use of anticoagulants is associated with the risk of bleeding, and hence there is a limit on the amount of their usage. Moreover, anticoagulants have not yet been widely used because they are empirically known to be effective but the mechanism of their action remains unknown.

On the other hand, cell migration is an essential event in the vital activities of the human body and is involved in a wide range of events occurring in the human body, while it is also known to cause unfavorable results including cancer metastasis. In addition, other known events in which cell migration is involved include angiogenesis and wound healing, etc.

SUMMARY OF THE INVENTION

Under these circumstances, there has been a demand for the development of a cell migration regulator capable of promoting or inhibiting cell migration, a method for regulating cell migration, and a pharmaceutical composition comprising such a regulator, and so on.

The present invention has been made in consideration of the above situation and aims to provide a cell migration regulator (e.g., a cell migration promoter, a cell migration inhibitor), a method for regulating cell migration (e.g., a method for promoting cell migration, a method for inhibiting cell migration), a pharmaceutical composition comprising such a regulator (i.e., a pharmaceutical composition for promoting angiogenesis, for treating wounds or ulcers, for suppressing or inhibiting cancer metastasis, or for suppressing or inhibiting angiogenesis), as well as a method for promoting cell spreading, a method for maintaining an epithelial morphology of cells, a composition for promoting cell spreading, and a composition for maintaining an epithelial morphology of cells, and so on, as shown below.

(1) A cell migration regulator, which comprises a peptide, a derivative thereof, or a salt of the peptide or the derivative, wherein the peptide comprises the full-length blood coagulation factor IX, a segment derived from the full-length blood coagulation factor IX by removal of the trypsin domain, the light chain of blood coagulation factor IX, or the EGF1 domain of blood coagulation factor IX, or the EGF3 domain of the endothelial cell locus-1 protein.

(2) A cell migration regulator, which comprises a peptide shown in (a) or (b) below, a derivative thereof, or a salt of the peptide or the derivative:
  (a) a peptide which comprises the amino acid sequence shown in SEQ ID NO: 2, 4, 6, 8 or 12; or
  (b) a peptide which comprises an amino acid sequence with deletion, substitution or addition of one or several amino acids in the amino acid sequence shown in SEQ ID NO: 2, 4, 6, 8 or 12 and which has cell migration-regulating activity.

(3) A cell migration promoter, which comprises a peptide shown in (a) or (b) below, a derivative thereof, or a salt of the peptide or the derivative:
  (a) a peptide which comprises the amino acid sequence shown in SEQ ID NO: 6, 8 or 12; or
  (b) a peptide which comprises an amino acid sequence with deletion, substitution or addition of one or several amino acids in the amino acid sequence shown in SEQ ID NO: 6, 8 or 12 and which has cell migration-promoting activity.

(4) A cell migration inhibitor, which comprises a peptide shown in (a) or (b) below, a derivative thereof, or a salt of the peptide or the derivative:
  (a) a peptide which comprises the amino acid sequence shown in SEQ ID NO: 2, 4, 8 or 12; or
  (b) a peptide which comprises an amino acid sequence with deletion, substitution or addition of one or several amino acids in the amino acid sequence shown in SEQ ID NO: 2, 4, 8 or 12 and which has cell migration-inhibiting activity.

(5) A method for regulating cell migration, which comprises administering an animal subject with the regulator according to claim 1 or 2.

(6) A method for promoting cell migration, which comprises administering an animal subject with the promoter according to claim 3.

(7) A method for inhibiting cell migration, which comprises administering an animal subject with the inhibitor according to claim 4.

(8) A pharmaceutical composition, which comprises the regulator according to claim 1 or 2.

(9) A pharmaceutical composition for promoting angiogenesis, which comprises the promoter according to claim 3.

(10) A pharmaceutical composition for treating wounds or ulcers, which comprises the promoter according to claim 3.

(11) A pharmaceutical composition for suppressing or inhibiting cancer metastasis, which comprises the inhibitor according to claim 4.

(12) A pharmaceutical composition for suppressing or inhibiting angiogenesis, which comprises the inhibitor according to claim 4.

(13) A method for promoting cell spreading, which comprises using the promoter according to claim 3.

(14) A method for maintaining an epithelial morphology of cells, which comprises using the inhibitor according to claim 4.

In the above methods (13) and (14), the cells may be exemplified by cultured cells.

(15) A composition for promoting cell spreading, which comprises the promoter according to claim 3.
(16) A composition for maintaining an epithelial morphology of cells, which comprises the inhibitor according to claim 4.

In the above compositions (15) and (16), the cells may be exemplified by cultured cells.

The present invention enables the provision of a cell migration regulator capable of promoting or inhibiting cell migration, such as a cell migration promoter or inhibitor.

The cell migration regulator of the present invention can be used in pharmaceutical compositions, e.g., for promoting angiogenesis, for treating wounds or ulcers, for suppressing or inhibiting cancer metastasis, or for suppressing or inhibiting angiogenesis. In this regard, the cell migration regulator of the present invention is applicable in the medical and pharmaceutical fields and is significantly useful.

Moreover, the cell migration regulator of the present invention can also be used effectively in promoting spreading of cells (particularly cultured cells) through promotion of cell migration and/or in maintaining an epithelial morphology of cells (particularly cultured cells) through inhibition of cell migration.

BRIEF DESCRIPTION OF THE DRAWINGS

The patent or application file contains at least one color drawing. Copies of this patent or patent application publication with color drawings will be provided by the USPTO upon request and payment of the necessary fee.

DESCRIPTION OF EMBODIMENTS

Figure 1:
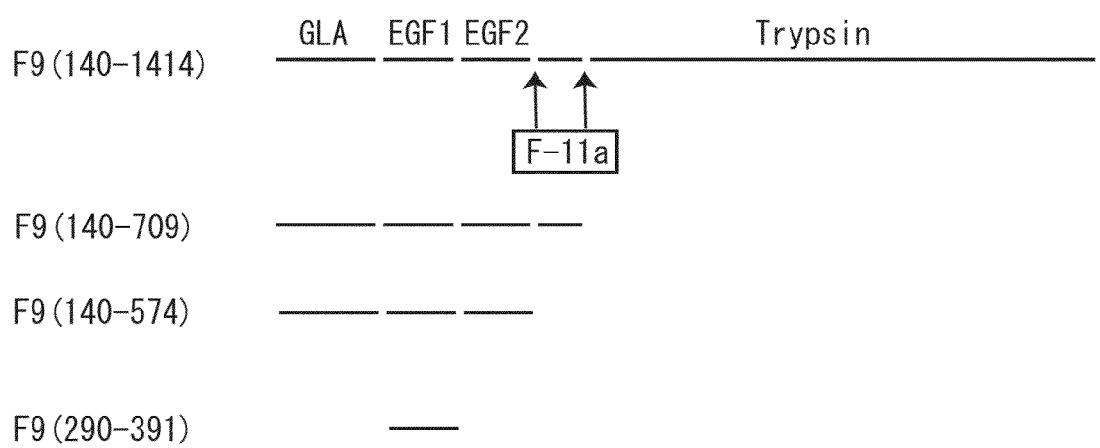
FIG. 1 shows the amino acid sequence structure constituting blood coagulation factor IX (F9). The numbers in the figure (e.g., 140-1414) are nucleotide numbers and represent regions in the nucleotide sequence of F9 (SEQ ID NO: 13; GenBank Accession No.: AK149372), which correspond to the respective amino acid sequence regions in F9. F9(140-1414) denotes a peptide consisting of the full-length F9 (whose definition is described later) (SEQ ID NO: 2); F9(140-709) denotes a peptide consisting of a segment derived from the full-length F9 by removal of the trypsin domain (i.e., the heavy chain of F9) (SEQ ID NO: 4); F9(140-574) denotes a peptide consisting of the light chain of F9 (SEQ ID NO: 6); and F9(290-391) denotes a peptide consisting of the EGF1 domain of F9 (F9-E1) (SEQ ID NO: 8) (the same applies hereinafter in the specification and drawings).

The present invention will be described in more detail below. The scope of the present invention is not limited by the following description, and any embodiments other than those illustrated below may also be carried out with appropriate modifications without departing from the spirit of the invention.

It should be noted that this specification incorporates the specification of Japanese Patent Application No. 2010-276777 (filed on Dec. 13, 2010) in its entirety, based on which the present application claims priority. Moreover, all publications cited herein, including prior art documents, patent gazettes and other patent documents, are incorporated herein by reference.

1. Summary of the Present Invention

The inventors of the present invention have found that blood coagulation factor IX (F9), which has been regarded as a protein contributing only to hemostatic coagulation, also has other important functions. More specifically, the inventors of the present invention have discovered that the light chain of F9, particularly the first EGF (EGF1; epidermal growth factor) domain of F9 (F9-E1) has activity to promote the migration ability of cells. This promoting activity appears when F9 is cleaved with blood coagulation factor XI (F11) into light and heavy chains, and so on (i.e., activated as a blood coagulation factor) during the process of coagulation reaction.

Moreover, the inventors of the present invention have also discovered that the third EGF (EGF3) domain (Del1-E3) of the endothelial cell locus-1 (Del-1; developmentally endothelial locus-1) protein, whose amino acid sequence is similar to that of F9-E1, also has effective promoting activity on cell migration ability. The Del-1 gene has been conventionally known to promote angiogenesis when introduced into ischemic animal models, although the degree of promotion was not sufficient. The effect of this gene therapy is not comparable to that of therapy with vascular endothelial growth factor (VEGF), which is a standard for angiogenic therapy, and it has not been elucidated by what mechanism angiogenesis proceeds. Thus, further technical development has been deemed to be impossible. Moreover, Del-1 is an insoluble protein which is deposited on the extracellular matrix, and hence the full-length Del-1 has been difficult to formulate due to its insolubility. In view of the foregoing, the finding that particularly Del1-E3 in the full-length Del-1 has excellent angiogenesis-promoting activity leads to an increase in the effect of the above gene therapy and also facilitates formulation because Del1-E3 is soluble as in the case of F9-E1.

On the other hand, the inventors of the present invention have also discovered that the full-length F9 before being activated as a blood coagulation factor has a completely opposite function, i.e., inhibits the migration ability of cells. This inhibiting activity on cell migration ability has also been observed in a segment derived from the full-length F9 by removal of the trypsin domain (i.e., the heavy chain of F9).

Further, the inventors of the present invention have clarified that F9-E1 and Del1-E3 with the above promoting activity each promote cell migration ability at low concentration, whereas they rather inhibit cell migration ability at high concentration. Namely, the inventors of the present invention have found that F9-E1 and Del1-E3 are capable of regulating cell migration ability, depending on their concentration used.

As described above, cell migration is an essential event for mammals, particularly the human body, and is involved in a wide range of events occurring in vivo, including angiogenesis, wound or ulcer healing process, cancer cell metastasis, etc. Thus, the above regulation (promotion or inhibition) of cell migration ability is effective in allowing angiogenic therapy (e.g., for arteriosclerotic ischemia such as myocardial infarction or cerebral infarction), treatment of wounds and ulcers, suppression or inhibition of cancer metastasis, as well as suppression or inhibition of angiogenesis, etc.

Moreover, the inventors of the present invention have found that it is also possible to effectively promote spreading of cells (particularly cultured cells) through promotion of cell migration or to effectively maintain an epithelial morphology of cells (particularly cultured cells) through inhibition of cell migration.

The present invention has been completed on the basis of the above findings.

2. Cell Migration Regulator

As described above, the cell migration regulator of the present invention (hereinafter referred to as the regulator of the present invention) comprises (i) a peptide comprising the full-length blood coagulation factor IX (F9), (ii) a peptide comprising a segment derived from the full-length F9 by removal of the trypsin domain (i.e., the heavy chain of F9), (iii) a peptide comprising the light chain of F9, or (iv) a peptide comprising the EGF1 domain of F9 (F9-E1), or (v) a peptide comprising the EGF3 domain (Del1-E3; one of the EGF similar domains) of the endothelial cell locus-1 (Del-1) protein.

The regulator of the present invention preferably comprises (i) a peptide consisting of the full-length F9, (ii) a peptide consisting of a segment derived from the full-length F9 by removal of the trypsin domain (i.e., the heavy chain of F9), (iii) a peptide consisting of the light chain of F9, or (iv) a peptide consisting of F9-E1, or (v) a peptide consisting of Del1-E3.

In the context of the present invention, the term "full-length F9" is intended to mean a peptide (protein) consisting of an amino acid sequence derived from the amino acid sequence of the entire F9 with a signal peptide and a propeptide (SEQ ID NO: 14; GenBank Accession No.: BAE28840) by removal of the signal peptide and propeptide segment. This signal peptide and propeptide segment is a region consisting of amino acids 1 to 46 in the amino acid sequence shown in SEQ ID NO: 14 (the same applies hereinafter in the specification). It should be noted that DNA encoding a peptide (protein) which consists of the amino acid sequence shown in SEQ ID NO: 14 corresponds to the nucleotide sequence shown in SEQ ID NO: 13 (GenBank Accession No.: AK149372).

Likewise, the full-length Del-1 protein consists of the amino acid sequence shown in SEQ ID NO: 10 and DNA encoding this Del-1 protein corresponds to the nucleotide sequence shown in SEQ ID NO: 9.

As described above, the regulator of the present invention more specifically comprises a peptide shown in (a) below:

(a) a peptide which comprises the amino acid sequence shown in SEQ ID NO: 2, 4, 6, 8 or 12.

The above peptide (a) is preferably, but is not limited to, a peptide consisting of the amino acid sequence shown in SEQ ID NO: 2, 4, 6, 8 or 12.

The amino acid sequences shown in SEQ ID NOs: 2, 4, 6, 8 and 12 correspond to (i) the amino acid sequence of the full-length F9 (SEQ ID NO: 2), (ii) the amino acid sequence of a segment derived from the full-length F9 by removal of the trypsin domain (i.e., the heavy chain of F9) (SEQ ID NO: 4), (iii) the amino acid sequence of the light chain of F9 (SEQ ID NO: 6), (iv) the amino acid sequence of F9-E1 (SEQ ID NO: 8) and (v) the amino acid sequence of Del1-E3 (SEQ ID NO: 12), respectively. It should be noted that the nucleotide sequences shown in SEQ ID NOs: 1, 3, 5, 7 and 11 correspond to DNAs encoding peptides which consist of the amino acid sequences shown in SEQ ID NOs: 2, 4, 6, 8 and 12, respectively, as will be described later.

The amino acid sequence shown in SEQ ID NO: 2 is a sequence consisting of amino acids 47 to 471 in the amino acid sequence shown in SEQ ID NO: 14, the amino acid sequence shown in SEQ ID NO: 4 is a sequence consisting of amino acids 47 to 236 in the amino acid sequence shown in SEQ ID NO: 14, the amino acid sequence shown in SEQ ID NO: 6 is a sequence consisting of amino acids 47 to 191 in the amino acid sequence shown in SEQ ID NO: 14, and the amino acid sequence shown in SEQ ID NO: 8 is a sequence consisting of amino acids 97 to 130 in the amino acid sequence shown in SEQ ID NO: 14.

Moreover, the amino acid sequence shown in SEQ ID NO: 12 is a sequence consisting of amino acids 123 to 157 in the amino acid sequence shown in SEQ ID NO: 10.

In the context of the present invention, the term "peptide" refers to a structure in which at least two or more amino acids are linked together via peptide bonds, including oligopeptides, polypeptides and so on. Moreover, a polypeptide formed into a certain three-dimensional structure is referred to as a protein, and such a protein also falls within the scope of the above "peptide" in the present invention. Thus, the peptide included in the regulator of the present invention may refer to any of an oligopeptide, a polypeptide and a protein.

Alternatively, as described above, the regulator of the present invention may comprise, as a peptide functionally equivalent to the above peptide (a), a peptide shown in (b) below:

(b) a peptide which comprises an amino acid sequence with deletion, substitution or addition of one or several amino acids in the amino acid sequence shown in SEQ ID NO: 2, 4, 6, 8 or 12 and which has cell migration-regulating activity.

In the context of the present invention, examples of the above "amino acid sequence with deletion, substitution or addition of one or several amino acids" include, but are not limited to, amino acid sequences with deletion, substitution or addition of 1 to 15 amino acids, 1 to 14 amino acids, 1 to 13 amino acids, 1 to 12 amino acids, 1 to 11 amino acids, 1 to 10 amino acids, 1 to 9 amino acids, 1 to 8 amino acids, 1 to 7 amino acids, 1 to 6 amino acids (one or several amino acids), 1 to 5 amino acids, 1 to 4 amino acids, 1 to 3 amino acids, 1 to 2 amino acids, or a single amino acid. In general, a smaller number is more preferred for the above deletion, substitution or addition of amino acids. Introduction of mutations such as deletion, substitution or addition as described above may be accomplished by using a kit for mutation introduction based on site-directed mutagenesis, including GeneTailor™ Site-Directed Mutagenesis Systems (Invitrogen) and TaKaRa Site-Directed Mutagenesis Systems (e.g., Mutan-K, Mutan-Super Express Km; Takara Bio Inc., Japan). Further, whether or not a peptide has the above mutation (i.e., deletion, substitution or addition) can be confirmed by using various techniques for amino acid sequencing, as well as X-ray or NMR-based structural analysis, etc.

Such a peptide functionally equivalent to the above peptide (a) may also be exemplified by a peptide which has an amino acid sequence sharing a homology of 80% or more with the amino acid sequence shown in SEQ ID NO: 2, 4, 6, 8 or 12 and which has cell migration-regulating activity. Examples of such a peptide include those which have an amino acid sequence sharing a homology of about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more with the amino acid sequence shown in SEQ ID NO: 2, 4, 6, 8 or 12 and which have cell migration-regulating activity. In general, a larger value is more preferred for the above homology.

In the context of the present invention, the term "cell migration-regulating activity" is intended to mean the promoting or inhibiting activity on cell migration ability, which may be measured, e.g., by Wound healing assay or Boyden chamber assay as described later in the Example section.

More specifically, the regulator of the present invention includes a cell migration promoter and a cell migration inhibitor.

The cell migration promoter of the present invention (hereinafter referred to as the promoter of the present invention) comprises a peptide shown in (a1) below:

(a1) a peptide which comprises the amino acid sequence shown in SEQ ID NO: 6, 8 or 12.

The above peptide (a1) is preferably, but is not limited to, a peptide consisting of the amino acid sequence shown in SEQ ID NO: 6, 8 or 12. The amino acid sequences shown in SEQ ID NOs: 6, 8 and 12 are each as described above.

Alternatively, the promoter of the present invention may comprise, as a peptide functionally equivalent to the above peptide (a1), a peptide shown in (b1) below:

(b1) a peptide which comprises an amino acid sequence with deletion, substitution or addition of one or several amino acids in the amino acid sequence shown in SEQ ID NO: 6, 8 or 12 and which has cell migration-promoting activity.

The same explanation as described above can also apply to the above "amino acid sequence with deletion, substitution or addition of one or several amino acids."

Such a peptide functionally equivalent to the above peptide (a1) may also be exemplified by a peptide which has an amino acid sequence sharing a homology of 80% or more with the amino acid sequence shown in SEQ ID NO: 6, 8 or 12 and which has cell migration-promoting activity. Examples of such a peptide include those which have an amino acid sequence sharing a homology of about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more with the amino acid sequence shown in SEQ ID NO: 6, 8 or 12 and which have cell migration-promoting activity. In general, a larger value is more preferred for the above homology.

In the present invention, cell migration-promoting activity may be measured, e.g., by Wound healing assay or Boyden chamber assay as described later in the Example section.

The cell migration inhibitor of the present invention (hereinafter referred to as the inhibitor of the present invention) comprises a peptide shown in (a2) below:

(a2) a peptide which comprises the amino acid sequence shown in SEQ ID NO: 2, 4, 8 or 12.

The above peptide (a2) is preferably, but is not limited to, a peptide consisting of the amino acid sequence shown in SEQ ID NO: 2, 4, 8 or 12. The amino acid sequences shown in SEQ ID NOs: 2, 4, 8 and 12 are each as described above.

Alternatively, the inhibitor of the present invention may comprise, as a peptide functionally equivalent to the above peptide (a2), a peptide shown in (b2) below:

(b2) a peptide which comprises an amino acid sequence with deletion, substitution or addition of one or several amino acids in the amino acid sequence shown in SEQ ID NO: 2, 4, 8 or 12 and which has cell migration-inhibiting activity.

The same explanation as described above can also apply to the above "amino acid sequence with deletion, substitution or addition of one or several amino acids."

Such a peptide functionally equivalent to the above peptide (a2) may be exemplified by a peptide which has an amino acid sequence sharing a homology of 80% or more with the amino acid sequence shown in SEQ ID NO: 2, 4, 8 or 12 and which has cell migration-inhibiting activity. Examples of such a peptide include those which have an amino acid sequence sharing a homology of about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, 99.9% or more with the amino acid sequence shown in SEQ ID NO: 2, 4, 8 or 12 and which have cell migration-inhibiting activity. In general, a larger value is more preferred for the above homology.

In the present invention, cell migration-inhibiting activity may be measured, e.g., by Wound healing assay or Boyden chamber assay as described later in the Example section.

It should be noted that a peptide comprising the amino acid sequence shown in SEQ ID NO: 8 or 12 can be included in both the promoter and inhibitor of the present invention described above. This is because these peptides function in both ways, i.e., are capable of promoting or inhibiting cell migration, depending on their concentration used, as will be described later. When used at low concentration, they have promoting activity on cell migration, whereas they have inhibiting activity on cell migration when used at high concentration.

The above peptides (a) and (b) included in the regulator of the present invention as well as the above peptides (a1), (a2), (b1) and (b2) included in the promoter and inhibitor of the present invention may be constructed from any number of amino acid residues. The number of amino acid residues may be selected as appropriate within a range that the peptides have their intended activity (regulating activity on cell migration, more specifically promoting or inhibiting activity on cell migration).

The above peptides (a) and (b) as well as the above peptides (a1), (a2), (b1) and (b2) may be either derived from natural products or artificially obtained by chemical synthesis. Without being limited thereto, preferred are peptides derived from natural products because they are often free from any adverse effects (e.g., cytotoxicity) and/or any side effects, etc.

Examples of peptides derived from natural products include naturally-occurring oligopeptides, polypeptides and proteins, or fragments thereof, etc. Such a peptide derived from a natural product may be obtained directly from the natural product by known collection and purification techniques or may be obtained by known gene recombination technology, in which a gene encoding this peptide is integrated into any of various expression vectors or the like and introduced into a cell to express the peptide, followed by known collection and purification techniques. Alternatively, such a peptide may be produced in a cell-free protein synthesis system using a commercially available kit (e.g., a reagent kit PROTEIOS™ (Toyobo Co., Ltd., Japan) or TNT™ System (Promega), a synthesizer PG-Mate™ (Toyobo Co., Ltd., Japan) or RTS (Roche Diagnostics)) and obtained by known collection and purification techniques. Peptides derived from natural products may be obtained in any way.

On the other hand, chemically synthesized peptides can be obtained by using known peptide synthesis techniques. Examples of synthesis techniques used for this purpose include azide method, acid chloride method, acid anhydride method, mixed acid anhydride method, DCC method, active ester method, carboimidazole method and oxidation-reduction method, etc. Moreover, their synthesis may be accomplished by applying either solid phase synthesis or liquid phase synthesis. A commercially available peptide synthesizer may also be used for this purpose. After synthesis reaction, the resulting peptides may be purified by using known purification techniques (e.g., chromatography) in combination.

The regulator, promoter and inhibitor of the present invention (hereinafter referred to as the regulator and others of the present invention) may comprise a derivative of the above peptide (a) or (b), (a1) or (b1), or (a2) or (b2) together with or instead of the peptide. Such a derivative is intended to encompass all derivatives which can be prepared from the above peptide, and examples include derivatives whose constituent amino acids are partially replaced with unnatural amino acids, and/or derivatives whose constituent amino acids (mainly side chains thereof) are partially chemically modified.

The regulator and others of the present invention may comprise a salt of the above peptide (a) or (b), (a1) or (b1), or (a2) or (b2), and/or a salt of a derivative of the peptide, together with or instead of the peptide and/or the derivative. Such a salt is preferably a physiologically acceptable acid addition salt or basic salt. Examples of such an acid addition salt include salts with inorganic acids (e.g., hydrochloric acid, phosphoric acid, hydrobromic acid, sulfuric acid), as well as salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid). Examples of such a basic salt include salts with inorganic bases (e.g., sodium hydroxide, potassium hydroxide, ammonium hydroxide, magnesium hydroxide), as well as salts with organic bases (e.g., caffeine, piperidine, trimethylamine, pyridine).

The salt intended in the present invention can be prepared using a suitable acid such as hydrochloric acid or a suitable base such as sodium hydroxide. For example, the salt can be prepared by treatment in water or in a fluid containing an inert water-miscible organic solvent (e.g., methanol, ethanol or dioxane) according to a standard protocol.

Without being limited thereto, the regulator and others of the present invention may consist of the above peptide (a) or (b), (a1) or (b1), or (a2) or (b2), a derivative thereof, or a salt of the peptide or the derivative, or may comprise the peptide, a derivative thereof, or a salt of the peptide or the derivative in combination with other components. Examples of other components include buffers such as PBS and Tris-HCl, as well as additives such as sodium azide and glycerol. In cases where the regulator and others of the present invention comprise other components, their content may be selected as appropriate within a range that does not significantly inhibit the regulating activity (promoting or inhibiting activity) on cell migration provided by the above peptide, a derivative thereof, or a salt of the peptide or the derivative. More specifically, in the case of using the above peptide in a solution state, the peptide concentration is preferably, but is not limited to, 0.3 ng/ml or higher, more preferably 0.3 to 5 ng/ml, even more preferably 0.3 to 2 ng/ml, still even more preferably 0.4 to 1.5 ng/ml, particularly preferably 0.6 to 1 ng/ml, and most preferably 0.8 to 1 ng/ml.

Target cells whose cell migration ability is to be regulated (promoted or inhibited) by the regulator and others of the present invention are not limited in any way and encompass various cells including vascular endothelial cells, fibroblasts, smooth muscle cells, tumor cells (cancer cells), and so on.

The present invention also provides a method for regulating cell migration by using the regulator of the present invention. Likewise, the present invention also provides a method for promoting or inhibiting cell migration by using the promoter or inhibitor of the present invention. These methods comprise the step of administering an animal subject with the regulator and others of the present invention, and may further comprise any other non-limiting step(s). Such an animal subject is not limited in any way and is exemplified by various mammals including humans or non-human animals, with humans being preferred. Although there is no limitation on the mode of administration, dosage regimen and dose of the regulator and others of the present invention, the modes of administration described later for pharmaceutical compositions can also apply as appropriate.

It should be noted that when an animal subject is administered in vivo with the regulator and others of the present invention, the above peptide (a) or (b) or the like serving as an active ingredient in the regulator of the present invention may be given in any way, either administered directly or introduced in a state of DNA encoding the peptide (gene transfer). DNA introduction may be accomplished by using various known techniques for gene transfer, including liposome method (lipoplex method), polyplex method, peptide method, electroporation, and virus vector method.

By using the regulator of the present invention, the present invention can also provide a method for promoting spreading of cells (particularly cultured cells) or a method for maintaining an epithelial morphology of cells (particularly cultured cells), etc. More specifically, it is possible to provide a method for promoting cell spreading by using the promoter of the present invention and a method for maintaining an epithelial morphology of cells by using the inhibitor of the present invention. In these methods, the regulator (promoter or inhibitor) of the present invention is preferably added directly to a culture solution of the target cells (cultured cells). For example, in the case of a method for promoting cell spreading, the concentration added in the culture solution is preferably about 0.1 to 10 ng/ml, and more preferably 0.1 to 5 ng/ml, while in the case of a method for maintaining an epithelial morphology of cells, the concentration added in the culture solution is preferably about 1 to 10 ng/ml, and more preferably 5 to 10 ng/ml (each being calculated as the peptide contained in the regulator of the present invention).

Further, the present invention also provides a composition for promoting cell spreading, which comprises the promoter of the present invention, and a composition for maintaining an epithelial morphology of cells, which comprises the inhibitor of the present invention.

In the context of the present invention, the phrase "spreading of cells (particularly cultured cells)" is intended to mean that cells grow, migrate and thereby spread across a culture vessel. Promoting cell spreading means that cells cover a wider area of a matrix within a shorter time.

Likewise, the phrase "epithelial morphology of cells (particularly cultured cells)" is intended to mean that cells adhere to each other in a cobblestone pattern to form a compact arrangement (morphology). Maintaining such an epithelial morphology means that cellular arrangement (morphology) in a cobblestone pattern is maintained against cell migration-promoting factors such as growth factors, cytokines, F9-E1, etc.

Cells (cultured cells) targeted for the above spreading promotion are not limited in any way, and preferred examples include vascular endothelial cells, keratinized epithelial cells, fibroblasts, induced pluripotent stem cells, etc. Likewise, cells (cultured cells) targeted for the above epithelial morphology maintenance are not limited in any way, and preferred examples include vascular endothelial cells, keratinized epithelial cells, induced pluripotent stem cells, etc.

A practical effect provided by the present invention as a result of promoting cell spreading lies, e.g., in reducing the period required to modify an artificial matrix with cells collected from the human body or processed cells thereof.

Likewise, a practical effect provided by the present invention as a result of maintaining an epithelial morphology of cells lies, e.g., in allowing epithelization of cells collected from the human body or processed cells thereof in a culture solution during modification of an artificial matrix with these cells.

3. DNA, Recombinant Vector, and Transformant (1) DNA

The present invention also contemplates DNA which comprises a nucleotide sequence encoding the above peptide (a) or (b), (a1) or (b1), or (a2) or (b2). Without being limited thereto, such DNA may consist of a nucleotide sequence encoding the peptide (more specifically consists of the nucleotide sequence shown in SEQ ID NO: 1, 3, 5, 7 or 11 described above) or may comprise this nucleotide sequence as a part thereof and additional known nucleotide sequences required for gene expression (e.g., transcription promoter, SD sequence, Kozak sequence, terminator). In the nucleotide sequence encoding the peptide, the type of codon is not limited in any way. For example, after transcription, it is possible to use codons generally used in mammals (e.g., humans) or codons generally used in microorganisms (e.g., $E.\ coli$ or yeast), plants or the like, which may be selected or designed as appropriate.

Moreover, the present invention also contemplates DNA which is hybridizable under stringent conditions with DNA consisting of a nucleotide sequence complementary to DNA comprising a nucleotide sequence encoding the above peptide (a) or (b), (a1) or (b1), or (a2) or (b2) and which encodes a protein having regulating (promoting or inhibiting) activity on cell migration. As used herein, the term "stringent conditions" refers to, for example, a salt (sodium) concentration of 150 to 900 mM and a temperature of 55° C. to 75° C., preferably a salt (sodium) concentration of 150 to 200 mM and a temperature of 60° C. to 70° C.

In addition to the foregoing, other hybridizable DNAs include those sharing a homology of about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with DNA consisting of the nucleotide sequence shown in SEQ ID NO: 1, 3, 5, 7 or 11 or with DNA encoding a peptide consisting of the amino acid sequence shown in SEQ ID NO: 2, 4, 6, 8 or 12, as calculated by homology search software such as FASTA or BLAST using default parameters.

(2) Recombinant Vector Comprising DNA

The present invention also contemplates a recombinant vector carrying the above DNA of the present invention ligated to (inserted into) an appropriate vector. The DNA of the present invention may be inserted into any vector capable of replicating in a host, and examples of such a vector include plasmid DNAs, phage DNAs, viruses, etc.

Examples of plasmid DNAs include $E.\ coli$-derived plasmids, $Bacillus\ subtilis$-derived plasmids, yeast-derived plasmids and so on, while examples of phage DNAs include λ phage and so on. Likewise, examples of viruses include adenoviruses and retroviruses, etc.

In addition to a promoter and the DNA of the present invention, the recombinant vector of the present invention may further comprise a cis element (e.g., enhancer), a splicing signal, a poly(A) addition signal, a ribosome binding sequence (SD sequence), a selection marker gene, a reporter gene and so on, if desired. It should be noted that examples of a selection marker gene include the dihydrofolate reductase gene, the ampicillin resistance gene, the neomycin resistance gene, etc. Examples of a reporter gene include genes for green fluorescent protein (GFP) or mutants thereof (fluorescent proteins such as EGFP, BFP and YFP), luciferase, alkaline phosphatase, LacZ, etc.

(3) Transformant

The present invention also contemplates a transformant obtainable by introducing the above recombinant vector of the present invention into a host such that a desired gene can be expressed. Any host may be used for this purpose as long as it is capable of expressing the DNA of the present invention, and it is possible to use bacteria, yeast and other microorganisms well known in the art, by way of example.

In the case of using a bacterium as a host, the recombinant vector of the present invention is not only autonomously replicable in the bacterium, but may also comprise a promoter, a ribosome binding sequence, the DNA of the present invention, and a transcription termination sequence. Examples of bacteria include *E. coli* (*Escherichia coli*) and so on. Examples of a promoter available for use include the lac promoter and so on. Techniques used for vector introduction into bacteria include various known introduction techniques, such as calcium ion method.

In the case of using yeast as a host, *Saccharomyces cerevisiae* or the like may be used, by way of example. In this case, any promoter may be used as long as it allows expression in yeast, and examples of such a promoter include the gall promoter and so on. Techniques used for vector introduction into yeast include, for example, electroporation, spheroplast method and so on.

4. Pharmaceutical Composition

The regulator and others of the present invention are useful as active ingredients in pharmaceutical compositions. It should be noted that the above peptide (a) or (b), (a1) or (b1), or (a2) or (b2) can also be referred to as the active ingredient.

Without being limited thereto, the pharmaceutical composition of the present invention is useful, e.g., as a pharmaceutical composition for promoting angiogenesis, for treating wounds or ulcers, for suppressing or inhibiting cancer (cancer cell) metastasis, or for suppressing or inhibiting angiogenesis. In particular, when the regulator of the present invention is a cell migration promoter, it is preferably used in pharmaceutical compositions for promoting angiogenesis (particularly for treating arteriosclerotic ischemic such as myocardial infarction or cerebral infarction) and for treating wounds or ulcers. When the regulator of the present invention is a cell migration inhibitor, it is preferably used in pharmaceutical compositions for suppressing or inhibiting cancer (cancer cell) metastasis and for suppressing or inhibiting angiogenesis.

The pharmaceutical composition of the present invention is preferably provided in the form of a pharmaceutical composition comprising the regulator and others of the present invention as an active ingredient and further comprising a pharmaceutically acceptable carrier.

The term "pharmaceutically acceptable carrier" is intended to include excipients, diluents, extenders, disintegrants, stabilizers, preservatives, buffering agents, emulsifiers, aromatics, coloring agents, sweeteners, thickeners, correctives, solubilizers, as well as other additives, etc. One or more such carriers may be used to prepare pharmaceutical compositions in the form of injections, solutions, capsules, suspensions, emulsions or syrups, etc. These pharmaceutical compositions may be administered orally or parenterally. Other dosage forms for parenteral administration include, for example, injections which comprise one or more active agents and are formulated in a routine manner. In the case of injections, they may be prepared by being dissolved or suspended in a pharmaceutically acceptable carrier such as physiological saline or commercially available injectable distilled water. In cases where the regulator and others of the present invention serving as active ingredients are administered in vivo, a colloidal dispersion system may also be used. Such a colloidal dispersion system can be expected to provide some effects, such as increased in vivo stability of the above peptide and/or efficient compound delivery to a specific organ, tissue or cell. The colloidal dispersion system is not limited in any way as long as it is commonly used, and examples include polyethylene glycol, polymer complexes, polymer assemblies, nanocapsules, microspheres, beads, as well as lipid-based dispersion systems including oil-in-water emulsions, micelles, mixed micelles and liposomes. Preferred are liposomes or artificial membrane vesicles which are effective in efficiently delivering a compound to a specific organ, tissue or cell.

The dose of the pharmaceutical composition of the present invention may vary depending on the age, sex, body weight and symptom of an animal subject (various mammals including humans or non-human animals, preferably humans), the intended therapeutic effect, the mode of administration, the time of treatment, or the type of the regulator and others of the present invention to be contained in the pharmaceutical composition, etc. In general, the pharmaceutical composition of the present invention may be administered, but not limited to, at a single dose ranging from 100 μg to 5000 mg per adult.

For example, when administered in the form of injections, the pharmaceutical composition of the present invention may be administered at a single dose of 100 μg to 100 mg per kg body weight of a human patient on an average of one to several times a day. The mode of administration includes intravenous injection, subcutaneous injection, intracutaneous injection, intramuscular injection or intraperitoneal injection, with intravenous injection being preferred. In some cases, injections may be prepared as non-aqueous dilutions (e.g., polyethylene glycol, vegetable oils such as olive oil, alcohols such as ethanol), suspensions or emulsions. Such injections may be sterilized, for example, by being filtered through a filter or mixed with a disinfectant. Injections may be prepared in reconstitutable form. Namely, injections may be converted into sterile solid compositions by lyophilization or other techniques, and the resulting solid compositions may be dissolved in sterile injectable distilled water or other solvents before use.

It should be noted that when a peptide comprising the amino acid sequence shown in SEQ ID NO: 8 or 12 (preferably a peptide consisting of this amino acid sequence) is used as a peptide included in the regulator and others of the present invention, the peptide concentration used is important because there are two cases where this peptide shows cell migration-promoting activity and where it shows cell migration-inhibiting activity, depending on its concentration used, as described above. For example, for cell migration-promoting activity, this peptide is administered to give a blood level of 0.1 ng/ml to 10 ng/ml, more preferably 0.1 ng/ml to 5 ng/ml, and even more preferably 0.1 ng/ml to 1 ng/ml. In contrast, for cell migration-inhibiting activity, this peptide is preferably administered to give a blood level of 100 ng/ml to 200 ng/ml, more preferably 100 ng/ml to 500 ng/ml, and even more preferably 100 ng/ml to 1000 ng/ml.

It should be noted that the present invention also provides the use of the regulator and others of the present invention (particularly the promoter of the present invention) for the manufacture of a pharmaceutical preparation (drug) for promoting angiogenesis. Moreover, the present invention also provides the regulator and others of the present invention (particularly the promoter of the present invention) for use in promoting angiogenesis. Further, the present invention provides a method for promoting angiogenesis, characterized in that the regulator and others of the present invention (particularly the promoter of the present invention) are used (i.e., administered to an animal subject), and also provides the use of the regulator and others of the present invention (particularly the promoter of the present invention) for promoting angiogenesis.

Likewise, the present invention also provides the use of the regulator and others of the present invention (particularly the promoter of the present invention) for the manufacture of a pharmaceutical preparation (drug) for treating wounds or ulcers. Moreover, the present invention also provides the regulator and others of the present invention (particularly the promoter of the present invention) for use in treating wounds or ulcers. Further, the present invention provides a method for treating wounds or ulcers, characterized in that the regulator and others of the present invention (particularly the promoter of the present invention) are used (i.e., administered to an animal subject), and also provides the use of the regulator and others of the present invention (particularly the promoter of the present invention) for treating wounds or ulcers.

The present invention also provides the use of the regulator and others of the present invention (particularly the inhibitor of the present invention) for the manufacture of a pharmaceutical preparation (drug) for suppressing or inhibiting cancer (cancer cell) metastasis. Moreover, the present invention also provides the regulator and others of the present invention (particularly the inhibitor of the present invention) for use in suppressing or inhibiting cancer (cancer cell) metastasis. Further, the present invention provides a method for suppressing or inhibiting cancer (cancer cell) metastasis, characterized in that the regulator and others of the present invention (particularly the inhibitor of the present invention) are used (i.e., administered to an animal subject), and also provides the use of the regulator and others of the present invention (particularly the inhibitor of the present invention) for suppressing or inhibiting cancer (cancer cell) metastasis.

The present invention also provides the use of the regulator and others of the present invention (particularly the inhibitor of the present invention) for the manufacture of a pharmaceutical preparation (drug) for suppressing or inhibiting angiogenesis. Moreover, the present invention also provides the regulator and others of the present invention (particularly the inhibitor of the present invention) for use in suppressing or inhibiting angiogenesis. Further, the present invention provides a method for suppressing or inhibiting angiogenesis, characterized in that the regulator and others of the present invention (particularly the inhibitor of the present invention) are used (i.e., administered to an animal subject), and also provides the use of the regulator and others of the present invention (particularly the inhibitor of the present invention) for suppressing or inhibiting angiogenesis.

5. Kit for Regulating Cell Migration

The present invention also provides a kit for regulating (promoting or inhibiting) cell migration, which comprises the regulator and others of the present invention as constituent members. The kit of the present invention can be used to promote or inhibit the migration ability of various cells and can be used effectively in, e.g., angiogenic therapy for arteriosclerotic ischemia, treatment of wounds or ulcers, suppression or inhibition of cancer metastasis, or suppression or inhibition of angiogenesis, etc. Thus, the kit of the present invention is also significantly useful in various experiments and researches in the medical and pharmaceutical fields. Moreover, the above kit of the present invention can also be used effectively in promoting spreading of cells (particularly cultured cells) or in maintaining an epithelial morphology of cells (particularly cultured cells).

The kit of the present invention may comprise the regulator and others of the present invention in combination with, but not limited to, various buffers, sterilized water, various reaction vessels (e.g., Eppendorf tubes), detergents, surfactants, various plates, antiseptics, various cell culture vessels, and an experimental manipulation manual (instruction manual), etc.

EXAMPLES

The present invention will be further described in more detail by way of the following examples, which are not intended to limit the scope of the present invention.

Reference Example 1

Structure of Blood Coagulation Factor IX Protein

As shown in FIG. 1, the amino acid sequence (SEQ ID NO: 2) constituting the full-length blood coagulation factor IX (F9) (F9(140-1414) in the figure) comprises, from the N-terminal side, the GLA domain and the downstream two EGF domains (EGF1, EGF2), on the C-terminal side of which the trypsin domain is linked via an amino acid sequence region composed of about 45 residues. During the progress of coagulation reaction, the amino acid sequence is cleaved at the sites indicated with arrows in FIG. 1 by the action of activated blood coagulation factor XI (F-11a in the figure) (to thereby remove the above amino acid sequence region composed of about 45 residues). The fragment N-terminal to the amino acid sequence region removed by cleavage is the light chain of F9, while the fragment C-terminal to the region is the heavy chain of F9 (i.e., the trypsin domain).

Example 1

Wound Healing Assay

Figure 2:
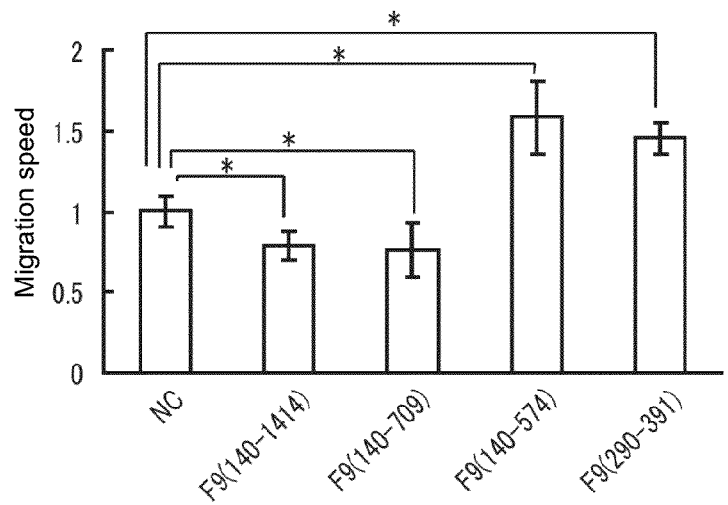
FIG. 2 shows the results of Wound healing assay. A: Results obtained for SCCKN cells (oral squamous cell carcinoma cell line). In comparison with the negative control (NC: AP alone), F9(140-1414) and F9(140-709) showed about a 20% inhibition of migration, while F9(140-574) and F9(290-391) showed about a 50% promotion of migration ability. B: Photographs showing the results in A above. Cells observed at 6 hours after addition of a conditioned medium (left panel: negative control (NC: AP alone); right panel: F9(140-574)). In comparison with the control, cells are separated away from each other and their arrangement (morphology) is also changed (scale bar in the photographs represents 100 μm). C: Similar results were obtained for Cos cells (monkey kidney cell line) (left panel) and P5 cells (mouse vascular endothelial cell line) (right panel) in the same assay. It should be noted that the numbers and expressions (e.g., 140-1414 and F9(140-1414)) appearing in FIGS. 2A to 2C have the same meanings as in FIG. 1.
Figure 2:
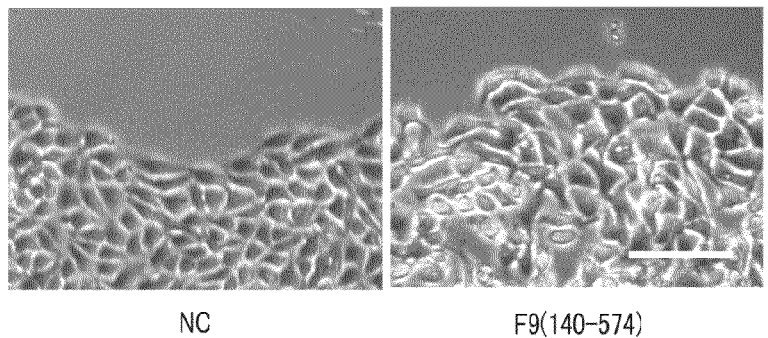
Figure 2:
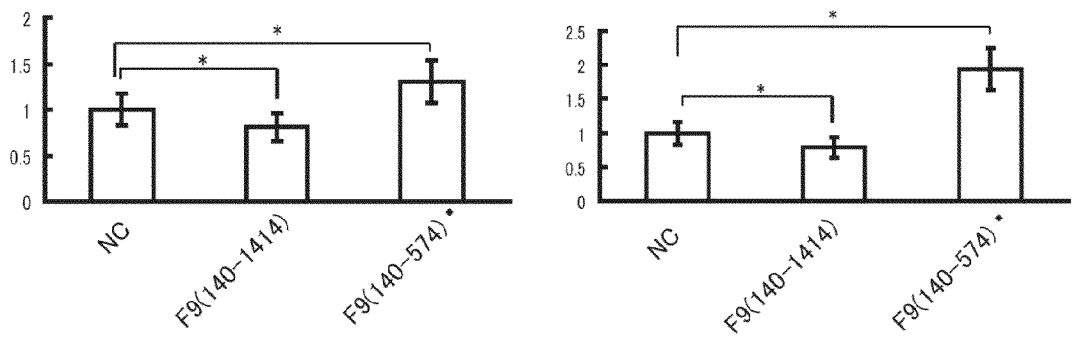

A plastic ring was placed in a 3 cm culture dish, and SCCKN cells (oral squamous cell carcinoma cell line) were seeded within the plastic ring and cultured for 24 hours. The ring was removed and the cells were imaged at one minute intervals. After observation for 6 hours in a normal culture solution, the culture solution was supplemented with alkaline phosphatase (AP; negative control) or a recombinant protein, i.e., AP-F9(140-1414), AP-F9(140-709), AP-F9(140-574) or AP-F9(290-391) (which is simply expressed as F9(140-1414), etc., in FIG. 2) at a concentration of 0.1 pmol/ml, followed by further observation. These recombinant proteins are fusion proteins between AP and the full-length F9 or a part thereof, each of which was prepared by constructing a recombinant vector where cDNA encoding a desired peptide (the full-length F9 or a part thereof) was inserted into an alkaline phosphatase (AP) expression vector (APtag4) to give a fusion gene with the AP gene by using known gene recombination technology and introducing the recombinant vector into CHO cells to express the fusion protein. It should be noted that the above cDNAs (more specifically those comprising DNAs consisting of the nucleotide sequences shown in SEQ ID NOs: 1, 3, 5 and 7) were each prepared for use as follows: primers were designed as appropriate based on the known gene sequence of F9 (SEQ ID NO: 13) and used in PCR to amplify a desired cDNA fragment, which was then integrated into APtag4. The moving images obtained above were analyzed for migration within 2 hours before and after addition of a conditioned medium. The front of the migrating cells was divided into 30 μm sections to calculate the mean value for the traveling distance of the front. Assuming that the migration speed before addition of the conditioned medium was set to 1, the migration speed after addition (mean±SEM) was expressed. The same assay was also repeated for Cos cells and P5 cells. The results obtained are shown in FIG. 2. $P<0.01$. It should be noted that the scale bar in the photographs of FIG. 2B represents 100 μm.

Example 2

Boyden Chamber Assay

Figure 3:
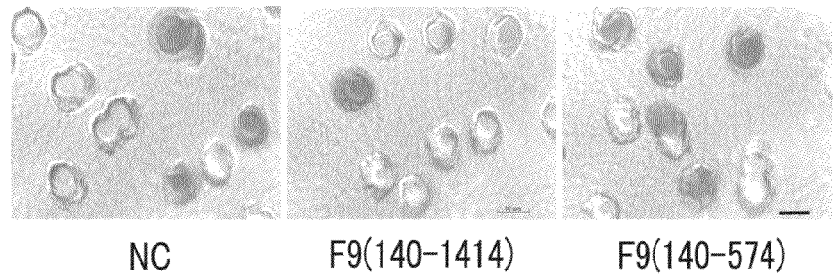
FIG. 3 shows the results of Boyden chamber assay. A: Appearance of SCCKN cells which have migrated. Cells having migrated into pores are stained in blue, while pores holding no cell are seen in white (scale bar in the photographs represents 10 μm). B: Graph showing the results in A above. In comparison with the control (NC: AP alone), F9(140-1414) and F9(140-709) showed about a 25% inhibition of migration, while F9(140-574) and F9(290-391) showed about an 80% promotion of migration ability. C: Similar results were obtained for Cos cells in the same assay. It should be noted that the numbers and expressions (e.g., 140-1414 and F9(140-1414)) appearing in FIGS. 3A to 3C have the same meanings as in FIG. 1.
Figure 3:
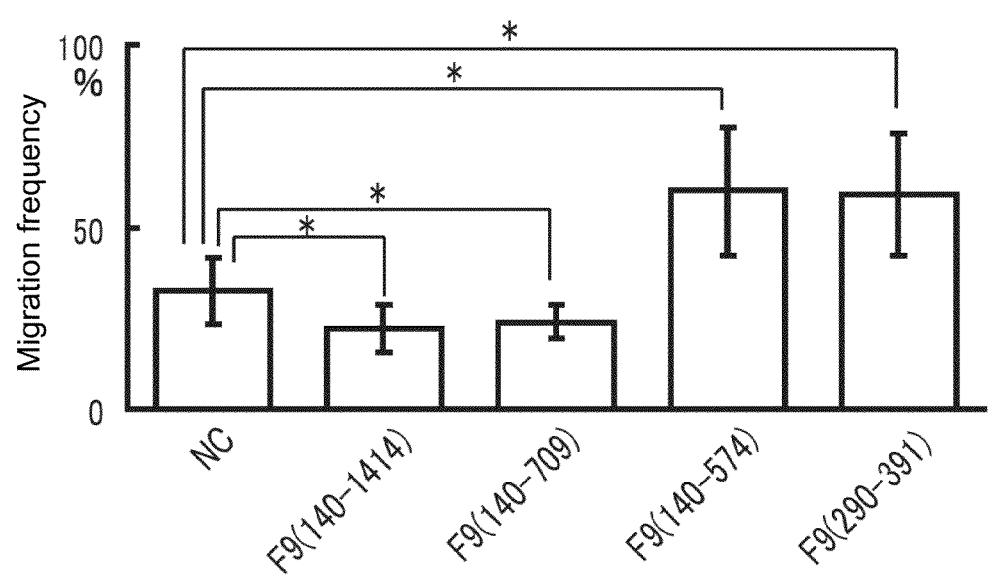
Figure 3:
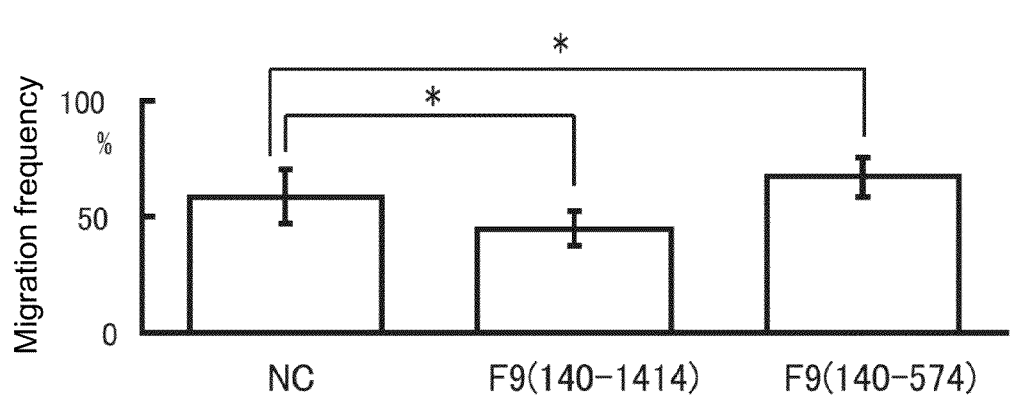

To evaluate cell migration ability by another assay different from the Wound healing assay used in Example 1, Boyden chamber assay was conducted with a Chemotaxicell (Kurabo Industries, Ltd., Japan). The recombinant proteins and negative control used in this assay, as well as their amounts added were the same as those in Example 1. The upper layer was charged with an excessive amount of cells (SCCKN cells or Cos cells) floating in a serum-free culture solution, while the lower layer was charged with a serum-containing normal culture solution, followed by culture for 30 minutes to 1 hour. After being fixed with 4% paraformaldehyde, the cells were stained with trypan blue and observed under a microscope to determine the ratio of pores holding the cells. The results obtained are shown in FIG. 3. It should be noted that the scale bar in the photographs of FIG. 3A represents 10 μm.

Reference Example 2

Homology Between F9 Structure and Del-1 Structure

Figure 4:
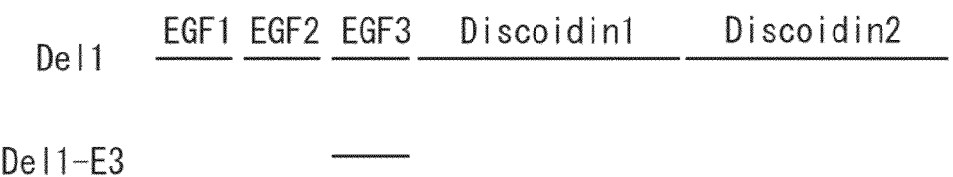
FIG. 4 shows homology between the structure of the EGF1 domain (F9-E1) in blood coagulation factor IX (F9) and the structure of the EGF3 domain (Del1-E3) in the endothelial cell locus-1 (Del-1; developmentally endothelial locus-1) protein. A: Position of Del1-E3 on the structure of Del-1. B: Homology between Del1-E3 (expressed as mDel1 in the figure) and F9-E1 (expressed as mF9 in the figure). The numbers in the figure (134, 145, 108, 119) represent amino acid residue numbers in Del-1 (SEQ ID NO: 10) or F9 (SEQ ID NO: 14).

As shown in FIG. 4, the amino acid sequence of Del-1 (SEQ ID NO: 10) is composed of, from the N-terminal side, three EGF domains (EGF1 to EGF3) and two discoidin domains (Discoidin1, Discoidin2) (FIG. 4A). The third EGF domain of Del-1 (Del1-E3) was found to share a consensus sequence with the EGF1 domain of F9 (F9-E1) (FIG. 4B).

Example 3

Wound Healing Assay

Figure 5:
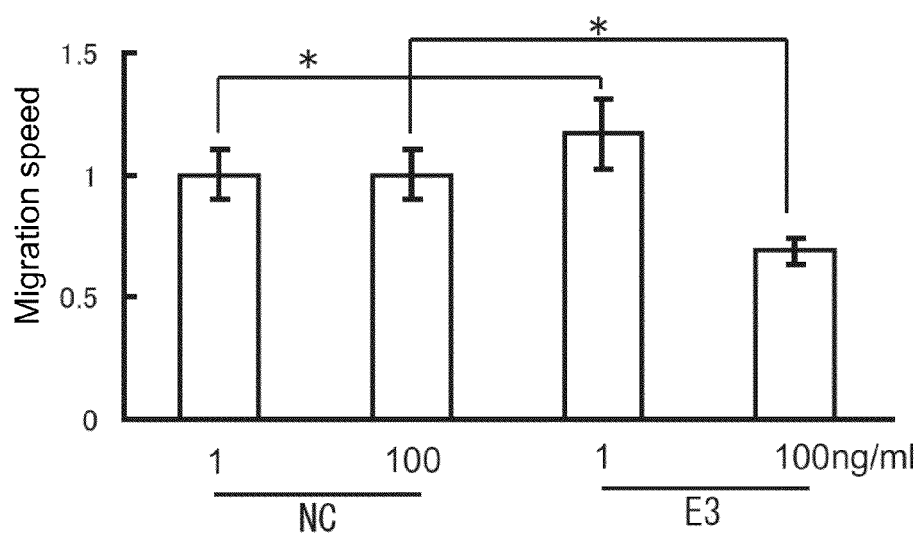
FIG. 5 shows the results of Wound healing assay. A: In comparison with the negative control (NC; CAT (chloramphenicol acetyl transferase) protein), Del1-E3 (expressed as E3 in the figure) promoted migration ability when added at a concentration of 1 ng/ml, but conversely inhibited migration ability at 100 ng/ml. B: Appearance of cells observed at 24 hours after addition of the recombinant protein (Del1-E3) (scale bar in the photographs represents 100 μm). In comparison with the negative control, the group receiving 1 ng/ml Del1-E3 (expressed as E3 in the figure) showed cell migration reaching a greater distance and wider intercellular gaps (i.e., promoted migration ability), whereas the group receiving 100 ng/ml Del1-E3 showed a shorter migration distance and a cellular appearance with branched and contracted processes (i.e., inhibited migration ability).
Figure 5:
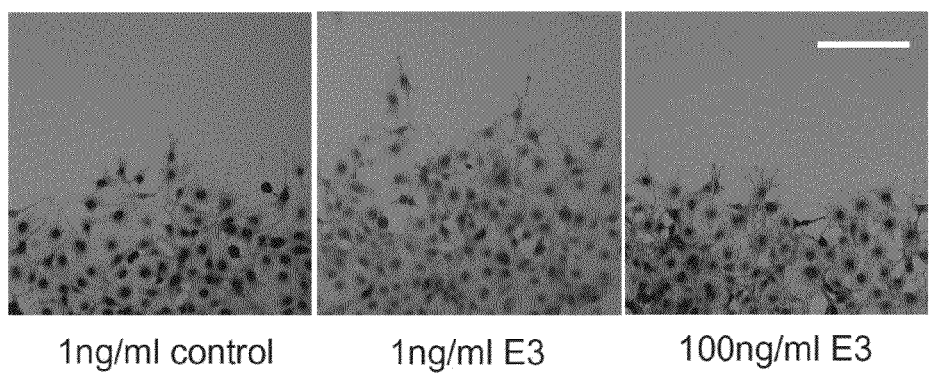

A plastic ring was placed in a 3 cm culture dish, and COS cells were seeded within the plastic ring and cultured for 24 hours. The ring was removed and the cells were imaged at one minute intervals. After observation for 6 hours in a normal culture solution, the culture solution was supplemented with 1 ng/ml CAT (chloramphenicol acetyl transferase) protein (negative control) or Del1-E3, followed by further observation. These recombinant proteins were prepared by introducing their recombinant DNAs into *E. coli* according to known gene recombination technology. The moving images obtained above were analyzed for migration within 2 hours before and after addition of a conditioned medium. The front of the migrating cells was divided into 30 μm sections to calculate the mean value for the traveling distance of the front. Assuming that the migration speed before addition of the conditioned medium was set to 1, the migration speed after addition (mean±SEM) was expressed. The results obtained are shown in FIG. 5. $P<0.01$. It should be noted that the scale bar in the photographs of FIG. 5B represents 100 μm.

INDUSTRIAL APPLICABILITY

Cell migration is involved in a wide range of events occurring in the human body. The present invention can be applied in the medical and pharmaceutical fields related to treatment of such events. For example, a peptide of F9-E1 can be prepared for use as a drug, and a gene encoding such a peptide can also be used for gene therapy. Examples of events in which migration is involved include angiogenesis, wound or ulcer healing process, cancer cell metastasis, etc. Thus, the present invention is useful in angiogenic therapy for arteriosclerotic ischemia, treatment of wounds or ulcers, suppression or inhibition of cancer metastasis, suppression or inhibition of angiogenesis, etc. Moreover, the present invention is also useful in promoting spreading of cells (particularly cultured cells) through promotion of cell migration or in maintaining an epithelial morphology of cells (particularly cultured cells) through inhibition of cell migration.

The invention claimed is:

1. A method for regulating cell migration, which comprises:
    injecting into a patient with an ulcer and/or cancer a liquid pharmaceutical composition comprising a liquid pharmaceutically acceptable carrier and dissolved, suspended or dispersed therein a pharmaceutically effective amount of one or more cell migration regulator peptides, which comprise:
    blood coagulation factor IX, blood coagulation factor IX heavy chain (heavy chain F9), blood coagulation factor IX light chain (light chain F9), blood coagulation factor IX Epithelial Growth Factor (EGF) 1 domain (F9-E1), or EGF3 domain of the developmentally endothelial cell locus-1 protein (Del1-E3), or a salt of any thereof,
    wherein the one or more cell migration regulator peptides are the sole active ingredients.

2. A method for regulating cell migration, which comprises:
    injecting into a patient with an ulcer and/or cancer a liquid pharmaceutical composition comprising a liquid pharmaceutically acceptable carrier and dissolved, suspended or dispersed therein a pharmaceutically effective amount of one or more cell migration regulator peptides, which comprise:
    amino acid sequences which are 98% or more identical to the amino acid sequence of SEQ ID NOS: 2, 4, 6, 8 and 12,
    wherein the one or more cell migration regulator peptides are the sole active ingredients.

3. A method for regulating cell migration, which comprises:
    administering to a patient with an ulcer and/or cancer a therapeutically effective amount of one or more cell migration regulator peptides, which comprises:
    blood coagulation factor IX, blood coagulation factor IX heavy chain (heavy chain F9), blood coagulation factor IX light chain (light chain F9), blood coagulation factor IX-Epithelial Growth Factor (EGF) 1 domain (F9-E1), or EGF3 domain of the developmentally endothelial cell locus-1 protein (Del1-E3), or a salt of any thereof,
    wherein the one or more of the cell migration regulator peptides are the sole active ingredients.

4. A method for regulating cell migration, which comprises:
    Administering to a patient with an ulcer and/or cancer a therapeutically effective amount of one or more cell migration regulator peptides, which comprise amino acid sequences which are 98% or more identical to the amino acid sequence of SEQ ID NOS: 2, 4, 6, 8 and 12,
    wherein one or more of the cell migration regulator peptides are the sole active ingredients.

5. The method of claim 1, 2, 3 or 4, wherein the one or more cell migration regulator peptides are administered in a dose of 100 µg to 100 mg per kg of body weight of a human patient one to several times per day.

6. The method of claim 1, 2, 3 or 4, wherein the one or more cell migration regulator peptides are administered to an adult patient at a dose ranging from 100 µg to 5000 mg.

* * * * *

SEQUENCE LISTING

```
<160> NUMBER OF SEQ ID NOS: 14

<210> SEQ ID NO 1
<211> LENGTH: 1275
<212> TYPE: DNA
<213> ORGANISM: Mus musculus
<220> FEATURE:
<221> NAME/KEY: CDS
<222> LOCATION: (1)..(1275)

<400> SEQUENCE: 1 tat aat tca gga aaa cta gaa gag ttt gtt cga gga aac ctt gaa aga      48
Tyr Asn Ser Gly Lys Leu Glu Glu Phe Val Arg Gly Asn Leu Glu Arg
1               5                   10                  15 gag tgt ata gaa gaa aga tgt agt ttt gaa gaa gca cga gaa gtt ttt      96
Glu Cys Ile Glu Glu Arg Cys Ser Phe Glu Glu Ala Arg Glu Val Phe
            20                  25                  30 gaa aac act gaa aaa act act gaa ttt tgg aag cag tat gtt gat gga     144
Glu Asn Thr Glu Lys Thr Thr Glu Phe Trp Lys Gln Tyr Val Asp Gly
        35                  40                  45 gat cag tgt gaa tca aat cct tgt tta aat ggt gga ata tgc aag gat     192
Asp Gln Cys Glu Ser Asn Pro Cys Leu Asn Gly Gly Ile Cys Lys Asp
    50                  55                  60
```

```
gat att agt tcc tat gaa tgc tgg tgc caa gtt gga ttt gaa gga agg    240
Asp Ile Ser Ser Tyr Glu Cys Trp Cys Gln Val Gly Phe Glu Gly Arg
 65                  70                  75                  80 aac tgt gaa tta gat gca acg tgt aac att aaa aat ggc agg tgc aag    288
Asn Cys Glu Leu Asp Ala Thr Cys Asn Ile Lys Asn Gly Arg Cys Lys
                 85                  90                  95 cag ttt tgt aaa aac agt cct gat aac aag gta att tgt tcc tgc act    336
Gln Phe Cys Lys Asn Ser Pro Asp Asn Lys Val Ile Cys Ser Cys Thr
             100                 105                 110 gag gga tac caa ctt gca gaa gac cag aag tcc tgt gaa cca aca gtt    384
Glu Gly Tyr Gln Leu Ala Glu Asp Gln Lys Ser Cys Glu Pro Thr Val
         115                 120                 125 cca ttt cca tgt ggg aga gct tct att tca tac agt tct aaa aag atc    432
Pro Phe Pro Cys Gly Arg Ala Ser Ile Ser Tyr Ser Ser Lys Lys Ile
     130                 135                 140 acg aga gct gag act gtt ttc tct aat atg gac tat gaa aat tct act    480
Thr Arg Ala Glu Thr Val Phe Ser Asn Met Asp Tyr Glu Asn Ser Thr
 145                 150                 155                 160 gaa gct gta ttc att caa gat gac atc act gat ggt gcc att ctt aat    528
Glu Ala Val Phe Ile Gln Asp Asp Ile Thr Asp Gly Ala Ile Leu Asn
                 165                 170                 175 aac gtc act gaa agt agt gaa tca ctt aat gac ttc act cga gtt gtt    576
Asn Val Thr Glu Ser Ser Glu Ser Leu Asn Asp Phe Thr Arg Val Val
             180                 185                 190 ggt gga gaa aac gca aaa ccg ggt caa atc cct tgg cag gtc att tta    624
Gly Gly Glu Asn Ala Lys Pro Gly Gln Ile Pro Trp Gln Val Ile Leu
         195                 200                 205 aat ggt gaa att gag gca ttc tgt gga ggt gcc atc att aat gaa aaa    672
Asn Gly Glu Ile Glu Ala Phe Cys Gly Gly Ala Ile Ile Asn Glu Lys
     210                 215                 220 tgg att gta act gct gcc cac tgt ctt aaa cct ggt gat aaa att gag    720
Trp Ile Val Thr Ala Ala His Cys Leu Lys Pro Gly Asp Lys Ile Glu
 225                 230                 235                 240 gtt gtt gct ggt gaa tat aac att gat aag aag gaa gac aca gaa caa    768
Val Val Ala Gly Glu Tyr Asn Ile Asp Lys Lys Glu Asp Thr Glu Gln
                 245                 250                 255 agg aga aat gtg att cga act atc cct cat cac cag tac aat gca act    816
Arg Arg Asn Val Ile Arg Thr Ile Pro His His Gln Tyr Asn Ala Thr
             260                 265                 270 att aat aag tat agt cat gac att gcc ttg ctg gaa ctg gat aaa cct    864
Ile Asn Lys Tyr Ser His Asp Ile Ala Leu Leu Glu Leu Asp Lys Pro
         275                 280                 285 tta ata cta aac agc tat gta aca cct atc tgt gtt gcc aat agg gaa    912
Leu Ile Leu Asn Ser Tyr Val Thr Pro Ile Cys Val Ala Asn Arg Glu
     290                 295                 300 tat aca aat atc ttc ctc aag ttt ggt tct ggc tat gtc agt ggc tgg    960
Tyr Thr Asn Ile Phe Leu Lys Phe Gly Ser Gly Tyr Val Ser Gly Trp
 305                 310                 315                 320 gga aaa gtc ttc aac aaa ggg aga cag gct tcc att ctt cag tac ctt   1008
Gly Lys Val Phe Asn Lys Gly Arg Gln Ala Ser Ile Leu Gln Tyr Leu
                 325                 330                 335 aga gtt cca ctg gtg gat aga gcc aca tgc ctt agg tcc aca aca ttc   1056
Arg Val Pro Leu Val Asp Arg Ala Thr Cys Leu Arg Ser Thr Thr Phe
             340                 345                 350 act atc tat aac aac atg ttc tgt gca ggc tac cgt gaa gga ggc aaa   1104
Thr Ile Tyr Asn Asn Met Phe Cys Ala Gly Tyr Arg Glu Gly Gly Lys
         355                 360                 365 gat tcg tgt gaa gga gat agt ggg gga ccc cat gtt act gaa gta gaa   1152
Asp Ser Cys Glu Gly Asp Ser Gly Gly Pro His Val Thr Glu Val Glu
     370                 375                 380
```

```
ggg aca agt ttc tta act ggc att att agc tgg ggt gaa gaa tgt gca      1200
Gly Thr Ser Phe Leu Thr Gly Ile Ile Ser Trp Gly Glu Glu Cys Ala
385                 390                 395                 400 atg aaa ggc aaa tat gga ata tat act aag gtt tcc cgg tac gtc aac      1248
Met Lys Gly Lys Tyr Gly Ile Tyr Thr Lys Val Ser Arg Tyr Val Asn
                405                 410                 415 tgg att aag gaa aaa aca aag cta act                                  1275
Trp Ile Lys Glu Lys Thr Lys Leu Thr
420                 425

<210> SEQ ID NO 2
<211> LENGTH: 425
<212> TYPE: PRT
<213> ORGANISM: Mus musculus

<400> SEQUENCE: 2

Tyr Asn Ser Gly Lys Leu Glu Glu Phe Val Arg Gly Asn Leu Glu Arg
1               5                   10                  15

Glu Cys Ile Glu Glu Arg Cys Ser Phe Glu Glu Ala Arg Glu Val Phe
            20                  25                  30

Glu Asn Thr Glu Lys Thr Thr Glu Phe Trp Lys Gln Tyr Val Asp Gly
        35                  40                  45

Asp Gln Cys Glu Ser Asn Pro Cys Leu Asn Gly Gly Ile Cys Lys Asp
    50                  55                  60

Asp Ile Ser Ser Tyr Glu Cys Trp Cys Gln Val Gly Phe Glu Gly Arg
65                  70                  75                  80

Asn Cys Glu Leu Asp Ala Thr Cys Asn Ile Lys Asn Gly Arg Cys Lys
                85                  90                  95

Gln Phe Cys Lys Asn Ser Pro Asp Asn Lys Val Ile Cys Ser Cys Thr
            100                 105                 110

Glu Gly Tyr Gln Leu Ala Glu Asp Gln Lys Ser Cys Glu Pro Thr Val
        115                 120                 125

Pro Phe Pro Cys Gly Arg Ala Ser Ile Ser Tyr Ser Ser Lys Lys Ile
    130                 135                 140

Thr Arg Ala Glu Thr Val Phe Ser Asn Met Asp Tyr Glu Asn Ser Thr
145                 150                 155                 160

Glu Ala Val Phe Ile Gln Asp Asp Ile Thr Asp Gly Ala Ile Leu Asn
                165                 170                 175

Asn Val Thr Glu Ser Ser Glu Ser Leu Asn Asp Phe Thr Arg Val Val
            180                 185                 190

Gly Gly Glu Asn Ala Lys Pro Gly Gln Ile Pro Trp Gln Val Ile Leu
        195                 200                 205

Asn Gly Glu Ile Glu Ala Phe Cys Gly Gly Ala Ile Ile Asn Glu Lys
    210                 215                 220

Trp Ile Val Thr Ala Ala His Cys Leu Lys Pro Gly Asp Lys Ile Glu
225                 230                 235                 240

Val Val Ala Gly Glu Tyr Asn Ile Asp Lys Lys Glu Asp Thr Glu Gln
                245                 250                 255

Arg Arg Asn Val Ile Arg Thr Ile Pro His His Gln Tyr Asn Ala Thr
            260                 265                 270

Ile Asn Lys Tyr Ser His Asp Ile Ala Leu Leu Glu Leu Asp Lys Pro
        275                 280                 285

Leu Ile Leu Asn Ser Tyr Val Thr Pro Ile Cys Val Ala Asn Arg Glu
    290                 295                 300
```

```
Tyr Thr Asn Ile Phe Leu Lys Phe Gly Ser Gly Tyr Val Ser Gly Trp
305                 310                 315                 320

Gly Lys Val Phe Asn Lys Gly Arg Gln Ala Ser Ile Leu Gln Tyr Leu
                325                 330                 335

Arg Val Pro Leu Val Asp Arg Ala Thr Cys Leu Arg Ser Thr Thr Phe
            340                 345                 350

Thr Ile Tyr Asn Asn Met Phe Cys Ala Gly Tyr Arg Glu Gly Gly Lys
        355                 360                 365

Asp Ser Cys Glu Gly Asp Ser Gly Gly Pro His Val Thr Glu Val Glu
    370                 375                 380

Gly Thr Ser Phe Leu Thr Gly Ile Ile Ser Trp Gly Glu Glu Cys Ala
385                 390                 395                 400

Met Lys Gly Lys Tyr Gly Ile Tyr Thr Lys Val Ser Arg Tyr Val Asn
                405                 410                 415

Trp Ile Lys Glu Lys Thr Lys Leu Thr
                420                 425

<210> SEQ ID NO 3
<211> LENGTH: 570
<212> TYPE: DNA
<213> ORGANISM: Mus musculus
<220> FEATURE:
<221> NAME/KEY: CDS
<222> LOCATION: (1)..(570)

<400> SEQUENCE: 3 tat aat tca gga aaa cta gaa gag ttt gtt cga gga aac ctt gaa aga      48
Tyr Asn Ser Gly Lys Leu Glu Glu Phe Val Arg Gly Asn Leu Glu Arg
1               5                   10                  15 gag tgt ata gaa gaa aga tgt agt ttt gaa gaa gca cga gaa gtt ttt      96
Glu Cys Ile Glu Glu Arg Cys Ser Phe Glu Glu Ala Arg Glu Val Phe
            20                  25                  30 gaa aac act gaa aaa act act gaa ttt tgg aag cag tat gtt gat gga     144
Glu Asn Thr Glu Lys Thr Thr Glu Phe Trp Lys Gln Tyr Val Asp Gly
        35                  40                  45 gat cag tgt gaa tca aat cct tgt tta aat ggt gga ata tgc aag gat     192
Asp Gln Cys Glu Ser Asn Pro Cys Leu Asn Gly Gly Ile Cys Lys Asp
    50                  55                  60 gat att agt tcc tat gaa tgc tgg tgc caa gtt gga ttt gaa gga agg     240
Asp Ile Ser Ser Tyr Glu Cys Trp Cys Gln Val Gly Phe Glu Gly Arg
65                  70                  75                  80 aac tgt gaa tta gat gca acg tgt aac att aaa aat ggc agg tgc aag     288
Asn Cys Glu Leu Asp Ala Thr Cys Asn Ile Lys Asn Gly Arg Cys Lys
                85                  90                  95 cag ttt tgt aaa aac agt cct gat aac aag gta att tgt tcc tgc act     336
Gln Phe Cys Lys Asn Ser Pro Asp Asn Lys Val Ile Cys Ser Cys Thr
            100                 105                 110 gag gga tac caa ctt gca gaa gac cag aag tcc tgt gaa cca aca gtt     384
Glu Gly Tyr Gln Leu Ala Glu Asp Gln Lys Ser Cys Glu Pro Thr Val
        115                 120                 125 cca ttt cca tgt ggg aga gct tct att tca tac agt tct aaa aag atc     432
Pro Phe Pro Cys Gly Arg Ala Ser Ile Ser Tyr Ser Ser Lys Lys Ile
    130                 135                 140 acg aga gct gag act gtt ttc tct aat atg gac tat gaa aat tct act     480
Thr Arg Ala Glu Thr Val Phe Ser Asn Met Asp Tyr Glu Asn Ser Thr
145                 150                 155                 160 gaa gct gta ttc att caa gat gac atc act gat ggt gcc att ctt aat     528
Glu Ala Val Phe Ile Gln Asp Asp Ile Thr Asp Gly Ala Ile Leu Asn
                165                 170                 175
```

```
aac gtc act gaa agt agt gaa tca ctt aat gac ttc act cga              570
Asn Val Thr Glu Ser Ser Glu Ser Leu Asn Asp Phe Thr Arg
            180                 185                 190

<210> SEQ ID NO 4
<211> LENGTH: 190
<212> TYPE: PRT
<213> ORGANISM: Mus musculus

<400> SEQUENCE: 4

Tyr Asn Ser Gly Lys Leu Glu Glu Phe Val Arg Gly Asn Leu Glu Arg
1               5                   10                  15

Glu Cys Ile Glu Glu Arg Cys Ser Phe Glu Glu Ala Arg Glu Val Phe
            20                  25                  30

Glu Asn Thr Glu Lys Thr Thr Glu Phe Trp Lys Gln Tyr Val Asp Gly
        35                  40                  45

Asp Gln Cys Glu Ser Asn Pro Cys Leu Asn Gly Gly Ile Cys Lys Asp
    50                  55                  60

Asp Ile Ser Ser Tyr Glu Cys Trp Cys Gln Val Gly Phe Glu Gly Arg
65                  70                  75                  80

Asn Cys Glu Leu Asp Ala Thr Cys Asn Ile Lys Asn Gly Arg Cys Lys
                85                  90                  95

Gln Phe Cys Lys Asn Ser Pro Asp Asn Lys Val Ile Cys Ser Cys Thr
            100                 105                 110

Glu Gly Tyr Gln Leu Ala Glu Asp Gln Lys Ser Cys Glu Pro Thr Val
        115                 120                 125

Pro Phe Pro Cys Gly Arg Ala Ser Ile Ser Tyr Ser Ser Lys Lys Ile
    130                 135                 140

Thr Arg Ala Glu Thr Val Phe Ser Asn Met Asp Tyr Glu Asn Ser Thr
145                 150                 155                 160

Glu Ala Val Phe Ile Gln Asp Asp Ile Thr Asp Gly Ala Ile Leu Asn
                165                 170                 175

Asn Val Thr Glu Ser Ser Glu Ser Leu Asn Asp Phe Thr Arg
            180                 185                 190

<210> SEQ ID NO 5
<211> LENGTH: 435
<212> TYPE: DNA
<213> ORGANISM: Mus musculus
<220> FEATURE:
<221> NAME/KEY: CDS
<222> LOCATION: (1)..(435)

<400> SEQUENCE: 5 tat aat tca gga aaa cta gaa gag ttt gtt cga gga aac ctt gaa aga     48
Tyr Asn Ser Gly Lys Leu Glu Glu Phe Val Arg Gly Asn Leu Glu Arg
1               5                   10                  15 gag tgt ata gaa gaa aga tgt agt ttt gaa gaa gca cga gaa gtt ttt     96
Glu Cys Ile Glu Glu Arg Cys Ser Phe Glu Glu Ala Arg Glu Val Phe
            20                  25                  30 gaa aac act gaa aaa act act gaa ttt tgg aag cag tat gtt gat gga    144
Glu Asn Thr Glu Lys Thr Thr Glu Phe Trp Lys Gln Tyr Val Asp Gly
        35                  40                  45 gat cag tgt gaa tca aat cct tgt tta aat ggt gga ata tgc aag gat    192
Asp Gln Cys Glu Ser Asn Pro Cys Leu Asn Gly Gly Ile Cys Lys Asp
    50                  55                  60 gat att agt tcc tat gaa tgc tgg tgc caa gtt gga ttt gaa gga agg    240
Asp Ile Ser Ser Tyr Glu Cys Trp Cys Gln Val Gly Phe Glu Gly Arg
65                  70                  75                  80
```

```
aac tgt gaa tta gat gca acg tgt aac att aaa aat ggc agg tgc aag      288
Asn Cys Glu Leu Asp Ala Thr Cys Asn Ile Lys Asn Gly Arg Cys Lys
                 85                  90                  95 cag ttt tgt aaa aac agt cct gat aac aag gta att tgt tcc tgc act      336
Gln Phe Cys Lys Asn Ser Pro Asp Asn Lys Val Ile Cys Ser Cys Thr
                100                 105                 110 gag gga tac caa ctt gca gaa gac cag aag tcc tgt gaa cca aca gtt      384
Glu Gly Tyr Gln Leu Ala Glu Asp Gln Lys Ser Cys Glu Pro Thr Val
                115                 120                 125 cca ttt cca tgt ggg aga gct tct att tca tac agt tct aaa aag atc      432
Pro Phe Pro Cys Gly Arg Ala Ser Ile Ser Tyr Ser Ser Lys Lys Ile
130                 135                 140 acg                                                                   435
Thr
145

<210> SEQ ID NO 6
<211> LENGTH: 145
<212> TYPE: PRT
<213> ORGANISM: Mus musculus

<400> SEQUENCE: 6

Tyr Asn Ser Gly Lys Leu Glu Glu Phe Val Arg Gly Asn Leu Glu Arg
1               5                   10                  15

Glu Cys Ile Glu Glu Arg Cys Ser Phe Glu Glu Ala Arg Glu Val Phe
            20                  25                  30

Glu Asn Thr Glu Lys Thr Thr Glu Phe Trp Lys Gln Tyr Val Asp Gly
        35                  40                  45

Asp Gln Cys Glu Ser Asn Pro Cys Leu Asn Gly Gly Ile Cys Lys Asp
    50                  55                  60

Asp Ile Ser Ser Tyr Glu Cys Trp Cys Gln Val Gly Phe Glu Gly Arg
65                  70                  75                  80

Asn Cys Glu Leu Asp Ala Thr Cys Asn Ile Lys Asn Gly Arg Cys Lys
                85                  90                  95

Gln Phe Cys Lys Asn Ser Pro Asp Asn Lys Val Ile Cys Ser Cys Thr
            100                 105                 110

Glu Gly Tyr Gln Leu Ala Glu Asp Gln Lys Ser Cys Glu Pro Thr Val
        115                 120                 125

Pro Phe Pro Cys Gly Arg Ala Ser Ile Ser Tyr Ser Ser Lys Lys Ile
    130                 135                 140

Thr
145

<210> SEQ ID NO 7
<211> LENGTH: 102
<212> TYPE: DNA
<213> ORGANISM: Mus musculus
<220> FEATURE:
<221> NAME/KEY: CDS
<222> LOCATION: (1)..(102)

<400> SEQUENCE: 7 tgt gaa tca aat cct tgt tta aat ggt gga ata tgc aag gat gat att       48
Cys Glu Ser Asn Pro Cys Leu Asn Gly Gly Ile Cys Lys Asp Asp Ile
1               5                   10                  15 agt tcc tat gaa tgc tgg tgc caa gtt gga ttt gaa gga agg aac tgt       96
Ser Ser Tyr Glu Cys Trp Cys Gln Val Gly Phe Glu Gly Arg Asn Cys
            20                  25                  30 gaa tta                                                              102
Glu Leu
```

<210> SEQ ID NO 8
<211> LENGTH: 34
<212> TYPE: PRT
<213> ORGANISM: Mus musculus

<400> SEQUENCE: 8

Cys Glu Ser Asn Pro Cys Leu Asn Gly Gly Ile Cys Lys Asp Asp Ile
1               5                   10                  15

Ser Ser Tyr Glu Cys Trp Cys Gln Val Gly Phe Glu Gly Arg Asn Cys
            20                  25                  30

Glu Leu

<210> SEQ ID NO 9
<211> LENGTH: 2303
<212> TYPE: DNA
<213> ORGANISM: Mus musculus
<220> FEATURE:
<221> NAME/KEY: CDS
<222> LOCATION: (619)..(2061)

<400> SEQUENCE: 9
gaattccggt taactgagga caaagggtaa tgcagaagtg atatttgatt tccattctca      60
ttcccagtgg ccttgatatt taaactgatt cctgccacca ggtccttggg ccaccctgtc     120
cctgcgtctc atatttctgc atgctgcttt gtttgtatat agtgcgctcc tggcctcagg     180
ctcgctcccc tccagctctc gcttcattgt tctccaagtc agaagccccc gcatccgccg     240
cgcagcagcg tgagccgtag tcactgctgg ccgcttcgcc tgcgtgcgcg cacggaaatc     300
ggggagccag gaacccaagg agccgccgtc cgcccgctgt gcctctgcta gaccactcgc     360
agccccagcc tctctcaagc gcacccacct ccgcgcaccc cagctcaggc gaagctggag     420
tgagggtgaa tcacccttc tctagggcca ccactctttt atcgcccttc ccaagatttg      480
agaagcgctg cgggaggaaa gacgtcctct tgatctctga cagggcgggg tttactgctg     540
tcctgcaggc gcgcctcgcc tactgtgccc tccgctacga ccccggacca gcccaggtca     600
cgtccgtgag aagggatc atg aag cac ttg gta gca gcc tgg ctt ttg gtt      651
                    Met Lys His Leu Val Ala Ala Trp Leu Leu Val
                    1               5                   10 gga ctc agc ctc ggg gtg ccc cag ttc ggc aaa ggt gac att tgc aac      699
Gly Leu Ser Leu Gly Val Pro Gln Phe Gly Lys Gly Asp Ile Cys Asn
            15                  20                  25 ccg aac ccc tgt gaa aat ggt ggc atc tgt ctg tca gga ctg gct gat      747
Pro Asn Pro Cys Glu Asn Gly Gly Ile Cys Leu Ser Gly Leu Ala Asp
        30                  35                  40 gat tcc ttt tcc tgt gag tgt cca gaa ggc ttc gca ggt ccg aac tgc      795
Asp Ser Phe Ser Cys Glu Cys Pro Glu Gly Phe Ala Gly Pro Asn Cys
    45                  50                  55 tct agt gtt gtg gag gtt gca tca gat gaa gaa aag cct act tca gca      843
Ser Ser Val Val Glu Val Ala Ser Asp Glu Glu Lys Pro Thr Ser Ala
60                  65                  70                  75 ggt ccc tgc atc cct aac cca tgc cat aac gga gga acc tgt gag ata      891
Gly Pro Cys Ile Pro Asn Pro Cys His Asn Gly Gly Thr Cys Glu Ile
                80                  85                  90 agc gaa gcc tat cga gga gac aca ttc ata ggc tat gtt tgt aaa tgt      939
Ser Glu Ala Tyr Arg Gly Asp Thr Phe Ile Gly Tyr Val Cys Lys Cys
            95                  100                 105 cct cgg gga ttt aat ggg att cac tgt cag cac aat ata aat gaa tgt      987
Pro Arg Gly Phe Asn Gly Ile His Cys Gln His Asn Ile Asn Glu Cys
        110                 115                 120

```
gaa gct gag cct tgc aga aat ggc gga ata tgt acc gac ctt gtt gct    1035
Glu Ala Glu Pro Cys Arg Asn Gly Gly Ile Cys Thr Asp Leu Val Ala
125                 130                 135 aac tac tct tgt gaa tgc cca gga gaa ttt atg gga cga aat tgt caa    1083
Asn Tyr Ser Cys Glu Cys Pro Gly Glu Phe Met Gly Arg Asn Cys Gln
140                 145                 150                 155 tat aaa tgc tct ggg cca ttg gga atc gaa ggt ggg atc ata tct aat    1131
Tyr Lys Cys Ser Gly Pro Leu Gly Ile Glu Gly Gly Ile Ile Ser Asn
                160                 165                 170 cag caa atc aca gct tca tct act cac cga gct ctt ttt gga ctc cgg    1179
Gln Gln Ile Thr Ala Ser Ser Thr His Arg Ala Leu Phe Gly Leu Arg
            175                 180                 185 aag tgg tat ccc tac tat gct cga ctt aat aag aag ggc ctt ata aat    1227
Lys Trp Tyr Pro Tyr Tyr Ala Arg Leu Asn Lys Lys Gly Leu Ile Asn
        190                 195                 200 gcc tgg aca gct gct gaa aat gac aga tgg cca tgg att cag ata aat    1275
Ala Trp Thr Ala Ala Glu Asn Asp Arg Trp Pro Trp Ile Gln Ile Asn
205                 210                 215 ttg caa aga aaa atg aga gtc act ggt gtt att acc caa gga gca aaa    1323
Leu Gln Arg Lys Met Arg Val Thr Gly Val Ile Thr Gln Gly Ala Lys
220                 225                 230                 235 agg att gga agc cca gag tac ata aaa tcc tac aaa att gcc tac agc    1371
Arg Ile Gly Ser Pro Glu Tyr Ile Lys Ser Tyr Lys Ile Ala Tyr Ser
                240                 245                 250 aat gac ggg aag acc tgg gca atg tac aaa gta aaa ggc acc aat gaa    1419
Asn Asp Gly Lys Thr Trp Ala Met Tyr Lys Val Lys Gly Thr Asn Glu
            255                 260                 265 gag atg gtc ttt cgt gga aat gtt gat aac aac aca cca tat gct aat    1467
Glu Met Val Phe Arg Gly Asn Val Asp Asn Asn Thr Pro Tyr Ala Asn
        270                 275                 280 tct ttc aca ccc cca atc aaa gct cag tat gta aga ctc tac ccc caa    1515
Ser Phe Thr Pro Pro Ile Lys Ala Gln Tyr Val Arg Leu Tyr Pro Gln
285                 290                 295 att tgt cga agg cat tgt act tta aga atg gaa ctt ctt ggc tgt gag    1563
Ile Cys Arg Arg His Cys Thr Leu Arg Met Glu Leu Leu Gly Cys Glu
300                 305                 310                 315 ctc tca ggc tgt tca gaa cct ttg ggg atg aaa tca ggg cat ata caa    1611
Leu Ser Gly Cys Ser Glu Pro Leu Gly Met Lys Ser Gly His Ile Gln
                320                 325                 330 gac tac cag atc act gcc tcc agc gtc ttc aga aca ctc aac atg gac    1659
Asp Tyr Gln Ile Thr Ala Ser Ser Val Phe Arg Thr Leu Asn Met Asp
            335                 340                 345 atg ttt act tgg gaa cca agg aaa gcc agg ctg gac aag caa ggc aaa    1707
Met Phe Thr Trp Glu Pro Arg Lys Ala Arg Leu Asp Lys Gln Gly Lys
        350                 355                 360 gta aat gcc tgg act tcc ggc cat aac gac cag tca caa tgg tta cag    1755
Val Asn Ala Trp Thr Ser Gly His Asn Asp Gln Ser Gln Trp Leu Gln
365                 370                 375 gtt gat ctt ctt gtc cct act aag gtg aca ggc atc att aca caa gga    1803
Val Asp Leu Leu Val Pro Thr Lys Val Thr Gly Ile Ile Thr Gln Gly
380                 385                 390                 395 gct aaa gat ttt ggt cac gtg cag ttt gtt ggg tca tac aaa cta gct    1851
Ala Lys Asp Phe Gly His Val Gln Phe Val Gly Ser Tyr Lys Leu Ala
                400                 405                 410 tac agc aat gat gga gaa cac tgg atg gtg cac cag gat gaa aaa cag    1899
Tyr Ser Asn Asp Gly Glu His Trp Met Val His Gln Asp Glu Lys Gln
            415                 420                 425
```

-continued

```
agg aaa gac aag gtt ttt caa ggc aat ttt gac aat gac act cac agg      1947
Arg Lys Asp Lys Val Phe Gln Gly Asn Phe Asp Asn Asp Thr His Arg
        430             435             440 aaa aat gtc atc gac cct ccc atc tat gca cga ttc ata aga atc ctt      1995
Lys Asn Val Ile Asp Pro Pro Ile Tyr Ala Arg Phe Ile Arg Ile Leu
    445             450             455 cct tgg tcc tgg tat gga agg atc act ctg cgg tca gag ctg ctg ggc      2043
Pro Trp Ser Trp Tyr Gly Arg Ile Thr Leu Arg Ser Glu Leu Leu Gly
460             465             470             475 tgc gca gag gag gaa tga agtgcggggc cgcacatccc acaatgcttt             2091
Cys Ala Glu Glu Glu
                480 tctttatttt cctataagta tctccacgaa atgaactgtg tgaagctgat ggaaactgca    2151 tttgttttt tcaaagtgtt caaattatgg taggctactg actgtctttt taggagttct    2211 aagcttgcct tttaataat ttaatttggt ttcctttgct caactctctt atgtaatatc     2271 acactgtctg tgagttactc ttcttgttct ct                                  2303

<210> SEQ ID NO 10
<211> LENGTH: 480
<212> TYPE: PRT
<213> ORGANISM: Mus musculus

<400> SEQUENCE: 10

Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Val Val Glu
    50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
        115                 120                 125

Arg Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

Pro Leu Gly Ile Glu Gly Gly Ile Ile Ser Asn Gln Gln Ile Thr Ala
                165                 170                 175

Ser Ser Thr His Arg Ala Leu Phe Gly Leu Arg Lys Trp Tyr Pro Tyr
            180                 185                 190

Tyr Ala Arg Leu Asn Lys Lys Gly Leu Ile Asn Ala Trp Thr Ala Ala
        195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255
```

```
Trp Ala Met Tyr Lys Val Lys Gly Thr Asn Glu Met Val Phe Arg
            260                 265                 270

Gly Asn Val Asp Asn Thr Pro Tyr Ala Asn Ser Phe Thr Pro Pro
            275                 280                 285

Ile Lys Ala Gln Tyr Val Arg Leu Tyr Pro Gln Ile Cys Arg Arg His
290                 295                 300

Cys Thr Leu Arg Met Glu Leu Leu Gly Cys Glu Leu Ser Gly Cys Ser
305                 310                 315                 320

Glu Pro Leu Gly Met Lys Ser Gly His Ile Gln Asp Tyr Gln Ile Thr
                325                 330                 335

Ala Ser Ser Val Phe Arg Thr Leu Asn Met Asp Met Phe Thr Trp Glu
            340                 345                 350

Pro Arg Lys Ala Arg Leu Asp Lys Gln Gly Lys Val Asn Ala Trp Thr
            355                 360                 365

Ser Gly His Asn Asp Gln Ser Gln Trp Leu Gln Val Asp Leu Leu Val
370                 375                 380

Pro Thr Lys Val Thr Gly Ile Ile Thr Gln Gly Ala Lys Asp Phe Gly
385                 390                 395                 400

His Val Gln Phe Val Gly Ser Tyr Lys Leu Ala Tyr Ser Asn Asp Gly
                405                 410                 415

Glu His Trp Met Val His Gln Asp Glu Lys Gln Arg Lys Asp Lys Val
                420                 425                 430

Phe Gln Gly Asn Phe Asp Asn Asp Thr His Arg Lys Asn Val Ile Asp
            435                 440                 445

Pro Pro Ile Tyr Ala Arg Phe Ile Arg Ile Leu Pro Trp Ser Trp Tyr
450                 455                 460

Gly Arg Ile Thr Leu Arg Ser Glu Leu Leu Gly Cys Ala Glu Glu Glu
465                 470                 475                 480

<210> SEQ ID NO 11
<211> LENGTH: 105
<212> TYPE: DNA
<213> ORGANISM: Mus musculus
<220> FEATURE:
<221> NAME/KEY: CDS
<222> LOCATION: (1)..(105)

<400> SEQUENCE: 11 tgt gaa gct gag cct tgc aga aat ggc gga ata tgt acc gac ctt gtt      48
Cys Glu Ala Glu Pro Cys Arg Asn Gly Gly Ile Cys Thr Asp Leu Val
1               5                   10                  15 gct aac tac tct tgt gaa tgc cca gga gaa ttt atg gga cga aat tgt      96
Ala Asn Tyr Ser Cys Glu Cys Pro Gly Glu Phe Met Gly Arg Asn Cys
                20                  25                  30 caa tat aaa                                                         105
Gln Tyr Lys
        35

<210> SEQ ID NO 12
<211> LENGTH: 35
<212> TYPE: PRT
<213> ORGANISM: Mus musculus

<400> SEQUENCE: 12

Cys Glu Ala Glu Pro Cys Arg Asn Gly Gly Ile Cys Thr Asp Leu Val
1               5                   10                  15

Ala Asn Tyr Ser Cys Glu Cys Pro Gly Glu Phe Met Gly Arg Asn Cys
                20                  25                  30
```

<210> SEQ ID NO 13
<211> LENGTH: 2735
<212> TYPE: DNA
<213> ORGANISM: Mus musculus
<220> FEATURE:
<221> NAME/KEY: CDS
<222> LOCATION: (2)..(1417)

<400> SEQUENCE: 13

```
g atg aag cac ctg aac acc gtc atg gca gaa tcc ccg gct ctc atc acc      49
  Met Lys His Leu Asn Thr Val Met Ala Glu Ser Pro Ala Leu Ile Thr
  1               5                  10                  15 atc ttc ctt tta gga tat cta ctc agt acc gaa tgt gca gtt ttc ctt        97
Ile Phe Leu Leu Gly Tyr Leu Leu Ser Thr Glu Cys Ala Val Phe Leu
             20                  25                  30 gat cgt gaa aat gcc acc aaa att ctt acc cgt cca aag aga tat aat       145
Asp Arg Glu Asn Ala Thr Lys Ile Leu Thr Arg Pro Lys Arg Tyr Asn
         35                  40                  45 tca gga aaa cta gaa gag ttt gtt cga gga aac ctt gaa aga gag tgt       193
Ser Gly Lys Leu Glu Glu Phe Val Arg Gly Asn Leu Glu Arg Glu Cys
 50                  55                  60 ata gaa gaa aga tgt agt ttt gaa gaa gca cga gaa gtt ttt gaa aac       241
Ile Glu Glu Arg Cys Ser Phe Glu Glu Ala Arg Glu Val Phe Glu Asn
 65                  70                  75                  80 act gaa aaa act act gaa ttt tgg aag cag tat gtt gat gga gat cag       289
Thr Glu Lys Thr Thr Glu Phe Trp Lys Gln Tyr Val Asp Gly Asp Gln
                 85                  90                  95 tgt gaa tca aat cct tgt tta aat ggt gga ata tgc aag gat gat att       337
Cys Glu Ser Asn Pro Cys Leu Asn Gly Gly Ile Cys Lys Asp Asp Ile
            100                 105                 110 agt tcc tat gaa tgc tgg tgc caa gtt gga ttt gaa gga agg aac tgt       385
Ser Ser Tyr Glu Cys Trp Cys Gln Val Gly Phe Glu Gly Arg Asn Cys
        115                 120                 125 gaa tta gat gca acg tgt aac att aaa aat ggc agg tgc aag cag ttt       433
Glu Leu Asp Ala Thr Cys Asn Ile Lys Asn Gly Arg Cys Lys Gln Phe
    130                 135                 140 tgt aaa aac agt cct gat aac aag gta att tgt tcc tgc act gag gga       481
Cys Lys Asn Ser Pro Asp Asn Lys Val Ile Cys Ser Cys Thr Glu Gly
145                 150                 155                 160 tac caa ctt gca gaa gac cag aag tcc tgt gaa cca aca gtt cca ttt       529
Tyr Gln Leu Ala Glu Asp Gln Lys Ser Cys Glu Pro Thr Val Pro Phe
                165                 170                 175 cca tgt ggg aga gct tct att tca tac agt tct aaa aag atc acg aga       577
Pro Cys Gly Arg Ala Ser Ile Ser Tyr Ser Ser Lys Lys Ile Thr Arg
            180                 185                 190 gct gag act gtt ttc tct aat atg gac tat gaa aat tct act gaa gct       625
Ala Glu Thr Val Phe Ser Asn Met Asp Tyr Glu Asn Ser Thr Glu Ala
        195                 200                 205 gta ttc att caa gat gac atc act gat ggt gcc att ctt aat aac gtc       673
Val Phe Ile Gln Asp Asp Ile Thr Asp Gly Ala Ile Leu Asn Asn Val
    210                 215                 220 act gaa agt agt gaa tca ctt aat gac ttc act cga gtt gtt ggt gga       721
Thr Glu Ser Ser Glu Ser Leu Asn Asp Phe Thr Arg Val Val Gly Gly
225                 230                 235                 240 gaa aac gca aaa ccg ggt caa atc cct tgg cag gtc att tta aat ggt       769
Glu Asn Ala Lys Pro Gly Gln Ile Pro Trp Gln Val Ile Leu Asn Gly
                245                 250                 255
```

-continued

| | |
|---|---|
| gaa att gag gca ttc tgt gga ggt gcc atc att aat gaa aaa tgg att<br>Glu Ile Glu Ala Phe Cys Gly Gly Ala Ile Ile Asn Glu Lys Trp Ile<br>260                          265                        270 | 817 |
| gta act gct gcc cac tgt ctt aaa cct ggt gat aaa att gag gtt gtt<br>Val Thr Ala Ala His Cys Leu Lys Pro Gly Asp Lys Ile Glu Val Val<br>275                          280                        285 | 865 |
| gct ggt gaa tat aac att gat aag aag gaa gac aca gaa caa agg aga<br>Ala Gly Glu Tyr Asn Ile Asp Lys Lys Glu Asp Thr Glu Gln Arg Arg<br>290                          295                        300 | 913 |
| aat gtg att cga act atc cct cat cac cag tac aat gca act att aat<br>Asn Val Ile Arg Thr Ile Pro His His Gln Tyr Asn Ala Thr Ile Asn<br>305                          310                        315                        320 | 961 |
| aag tat agt cat gac att gcc ttg ctg gaa ctg gat aaa cct tta ata<br>Lys Tyr Ser His Asp Ile Ala Leu Leu Glu Leu Asp Lys Pro Leu Ile<br>                        325                        330                        335 | 1009 |
| cta aac agc tat gta aca cct atc tgt gtt gcc aat agg gaa tat aca<br>Leu Asn Ser Tyr Val Thr Pro Ile Cys Val Ala Asn Arg Glu Tyr Thr<br>                        340                        345                        350 | 1057 |
| aat atc ttc ctc aag ttt ggt tct ggc tat gtc agt ggc tgg gga aaa<br>Asn Ile Phe Leu Lys Phe Gly Ser Gly Tyr Val Ser Gly Trp Gly Lys<br>                        355                        360                        365 | 1105 |
| gtc ttc aac aaa ggg aga cag gct tcc att ctt cag tac ctt aga gtt<br>Val Phe Asn Lys Gly Arg Gln Ala Ser Ile Leu Gln Tyr Leu Arg Val<br>370                          375                        380 | 1153 |
| cca ctg gtg gat aga gcc aca tgc ctt agg tcc aca aca ttc act atc<br>Pro Leu Val Asp Arg Ala Thr Cys Leu Arg Ser Thr Thr Phe Thr Ile<br>385                          390                        395                        400 | 1201 |
| tat aac aac atg ttc tgt gca ggc tac cgt gaa gga ggc aaa gat tcg<br>Tyr Asn Asn Met Phe Cys Ala Gly Tyr Arg Glu Gly Gly Lys Asp Ser<br>                        405                        410                        415 | 1249 |
| tgt gaa gga gat agt ggg gga ccc cat gtt act gaa gta gaa ggg aca<br>Cys Glu Gly Asp Ser Gly Gly Pro His Val Thr Glu Val Glu Gly Thr<br>                        420                        425                        430 | 1297 |
| agt ttc tta act ggc att att agc tgg ggt gaa gaa tgt gca atg aaa<br>Ser Phe Leu Thr Gly Ile Ile Ser Trp Gly Glu Glu Cys Ala Met Lys<br>                        435                        440                        445 | 1345 |
| ggc aaa tat gga ata tat act aag gtt tcc cgg tac gtc aac tgg att<br>Gly Lys Tyr Gly Ile Tyr Thr Lys Val Ser Arg Tyr Val Asn Trp Ile<br>450                          455                        460 | 1393 |
| aag gaa aaa aca aag cta act taa tgaaaaacct atttccaaag acaattcagt<br>Lys Glu Lys Thr Lys Leu Thr<br>465                          470 | 1447 |
| ggaattgaaa atgggtgatg ccctttacag actagtcttt ctaccttttg ttaaatttaa | 1507 |
| atatataagt tctacaaaca ctgattttc tctgtgcata agacaagccc atctaggatc | 1567 |
| tatattgttc tagagtaagt aggttagcaa atataatcac tagagaaata gtttagtaag | 1627 |
| agattcacca tttctgtaag tccagccctt gttaaaatta gaaagtaaag ctttccgtgt | 1687 |
| tgcccataag gcgtgatggt tcttgataca gagatgtacc caattctccc tccttggcag | 1747 |
| caattcatgt tttagctctt ccttgctact ctcaatttta ttagttttct atccagaatc | 1807 |
| tttaacccat ttatggccag aagaatacaa gagcagctga aaaattaaaa ctcatcaaaa | 1867 |
| gcatgacttc ctctcctgat tttctgaat cttgtatctt ttacaactcc caaccacaa | 1927 |
| atcactgacc tctccgtcat tctcacctte cctttctcca tcaccactga aggaggaagc | 1987 |
| tatatgagtt ccaggacagc ctaggtacac agagaaaccc ggtcttgaaa gaaaagagag | 2047 |
| agtgggagag agagagagagag gagagagagg agaaagaaat gattaattta | 2107 |
| atcatattgg taatatatat atattatatc tctaaaaaaa agtcactaaa ccttacttgt | 2167 |

-continued

```
aacaactgcc tatttctatg gtgtaaatat ccttactttg gtagatttca agctattaac    2227
atgaagttac tggaaaagga gttgagaaaa catatggaaa attactctta aaactgtttc    2287
aggcagtttt taacctagaa gcagctgaac tttctaggaa tacttcaaca gtgcatcttc    2347
agccttctcc agttccaacc tacctaaggg tcatgtctct cacagcaggc tcaaggctgc    2407
aagagtcatt gcaaatggcc aactgacttg cccatttatg gttttcttct caccggtaaa    2467
ctgttattgt aattaacact gtcatattga attttctaga gggatgctga ccatccgacc    2527
catttctcat ctgagacttg gtgaactggc attttaatac ttatctggac ctttgtagtg    2587
atgcataatt ggtttgaacc ccttgtcact gccacctgcc cccaccaaca caaaatccta    2647
cttcattact gctgactctg ctaacgttcc actacttgtt gcctcttttg tcttgcaaga    2707
agtatcaata aacatctttc cagatttc                                        2735

<210> SEQ ID NO 14
<211> LENGTH: 471
<212> TYPE: PRT
<213> ORGANISM: Mus musculus

<400> SEQUENCE: 14

Met Lys His Leu Asn Thr Val Met Ala Glu Ser Pro Ala Leu Ile Thr
1               5                   10                  15

Ile Phe Leu Leu Gly Tyr Leu Leu Ser Thr Glu Cys Ala Val Phe Leu
            20                  25                  30

Asp Arg Glu Asn Ala Thr Lys Ile Leu Thr Arg Pro Lys Arg Tyr Asn
        35                  40                  45

Ser Gly Lys Leu Glu Glu Phe Val Arg Gly Asn Leu Glu Arg Glu Cys
    50                  55                  60

Ile Glu Glu Arg Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ile Cys Lys Asp Asp Ile
            100                 105                 110

Ser Ser Tyr Glu Cys Trp Cys Gln Val Gly Phe Glu Gly Arg Asn Cys
        115                 120                 125

Glu Leu Asp Ala Thr Cys Asn Ile Lys Asn Gly Arg Cys Lys Gln Phe
    130                 135                 140

Cys Lys Asn Ser Pro Asp Asn Lys Val Ile Cys Ser Cys Thr Glu Gly
145                 150                 155                 160

Tyr Gln Leu Ala Glu Asp Gln Lys Ser Cys Glu Pro Thr Val Pro Phe
                165                 170                 175

Pro Cys Gly Arg Ala Ser Ile Ser Tyr Ser Ser Lys Lys Ile Thr Arg
            180                 185                 190

Ala Glu Thr Val Phe Ser Asn Met Asp Tyr Glu Asn Ser Thr Glu Ala
        195                 200                 205

Val Phe Ile Gln Asp Asp Ile Thr Asp Gly Ala Ile Leu Asn Asn Val
    210                 215                 220

Thr Glu Ser Ser Glu Ser Leu Asn Asp Phe Thr Arg Val Val Gly Gly
225                 230                 235                 240

Glu Asn Ala Lys Pro Gly Gln Ile Pro Trp Gln Val Ile Leu Asn Gly
                245                 250                 255

Glu Ile Glu Ala Phe Cys Gly Gly Ala Ile Ile Asn Glu Lys Trp Ile
            260                 265                 270
```

```
Val Thr Ala Ala His Cys Leu Lys Pro Gly Asp Lys Ile Glu Val Val
        275                 280                 285

Ala Gly Glu Tyr Asn Ile Asp Lys Lys Glu Asp Thr Glu Gln Arg Arg
    290                 295                 300

Asn Val Ile Arg Thr Ile Pro His His Gln Tyr Asn Ala Thr Ile Asn
305                 310                 315                 320

Lys Tyr Ser His Asp Ile Ala Leu Leu Glu Leu Asp Lys Pro Leu Ile
                325                 330                 335

Leu Asn Ser Tyr Val Thr Pro Ile Cys Val Ala Asn Arg Glu Tyr Thr
                340                 345                 350

Asn Ile Phe Leu Lys Phe Gly Ser Gly Tyr Val Ser Gly Trp Gly Lys
            355                 360                 365

Val Phe Asn Lys Gly Arg Gln Ala Ser Ile Leu Gln Tyr Leu Arg Val
    370                 375                 380

Pro Leu Val Asp Arg Ala Thr Cys Leu Arg Ser Thr Thr Phe Thr Ile
385                 390                 395                 400

Tyr Asn Asn Met Phe Cys Ala Gly Tyr Arg Glu Gly Gly Lys Asp Ser
                405                 410                 415

Cys Glu Gly Asp Ser Gly Gly Pro His Val Thr Glu Val Glu Gly Thr
                420                 425                 430

Ser Phe Leu Thr Gly Ile Ile Ser Trp Gly Glu Glu Cys Ala Met Lys
            435                 440                 445

Gly Lys Tyr Gly Ile Tyr Thr Lys Val Ser Arg Tyr Val Asn Trp Ile
    450                 455                 460

Lys Glu Lys Thr Lys Leu Thr
465                 470
```